United States Patent
Yang et al.

(10) Patent No.: US 6,824,712 B1
(45) Date of Patent: Nov. 30, 2004

(54) SELECTIVELY LIGHT-ABSORPTIVE MATERIAL, COATING COMPOSITION CONTAINING THE SAME, AND FILTER MANUFACTURED USING THE COATING COMPOSITION FOR COLOR DISPLAYS

(75) Inventors: Seung-gak Yang, Seoul (KR); Jin-bum Park, Chunghongbuk-do (KR); Geun-taek Bae, Chonan (KR); Ho-chan Lee, Chonan (KR)

(73) Assignee: SKC Co. Ltd., Suwon (CN)

( * ) Notice: Subject to any disclaimer, the term of this patent is extended or adjusted under 35 U.S.C. 154(b) by 219 days.

(21) Appl. No.: 10/048,075

(22) PCT Filed: Jul. 29, 2000

(86) PCT No.: PCT/KR00/00829

§ 371 (c)(1),
(2), (4) Date: Jan. 29, 2002

(87) PCT Pub. No.: WO01/10971

PCT Pub. Date: Feb. 15, 2001

(30) Foreign Application Priority Data

| Aug. 4, 1999 | (KR) | 1999-31991 |
| Aug. 4, 1999 | (KR) | 1999-31992 |
| May 29, 2000 | (KR) | 2000-28992 |
| Jul. 19, 2000 | (KR) | 2000-41426 |

(51) Int. Cl.$^7$ .............................. F21V 9/00; G02B 5/22
(52) U.S. Cl. ...................... 252/582; 252/587; 252/589; 359/885; 359/886; 540/121
(58) Field of Search .................. 540/121; 252/582, 252/587, 589; 359/885, 886

(56) References Cited

U.S. PATENT DOCUMENTS 2,681,345 A * 6/1954 France ....................... 540/121

(List continued on next page.)

FOREIGN PATENT DOCUMENTS

GB 1546223 A * 5/1979

(List continued on next page.)

*Primary Examiner*—Philip C. Tucker
(74) *Attorney, Agent, or Firm*—Nixon & Vanderhye, P.C.; Frank P. Presta

(57) ABSTRACT

A selectively light-absorptive material for a color display, comprising a tetrazaporphyrine derivative having the formula:

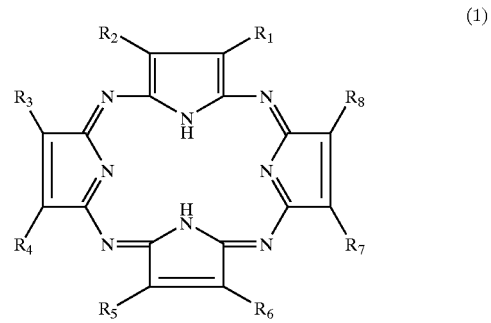

(1)

where $R_1$, $R_2$, $R_3$, $R_4$, $R_5$, $R_6$, $R_7$ and $R_8$ are independently selected from the group consisting of hydrogen; an unsubstituted phenyl group, an alkyl group; an alkoxy group; a nitro group; halogen atoms; a halide; a cyano group; an alkylamino group; an aminoalkyl group; and a phenyl group having a substitutent selected from an alkyl group, an alkoxy group, a nitro group, halogen atoms, a halide, an alkylamino group, an aminoalkyl group and a cyano group, or two neighboring substituents among $R_1$, $R_2$, $R_3$, $R_4$, $R_5$, $R_6$, $R_7$ and $R_8$ are fused and substituted with 1 to 3 aromatic cyclic compounds, and unsubstituted groups among $R_1$, $R_2$, $R_3$, $R_4$, $R_5$, $R_6$, $R_7$ and $R_8$ are independently selected from the group consisting of hydrogen, an alkyl group, an alkoxy group, an allyl group, halogen atoms, a halide, a cyano group and a nitro group. The material also comprises a plastic resin, an organic solvent and/or an infrared ray blocking agent.

6 Claims, 8 Drawing Sheets

U.S. PATENT DOCUMENTS

| | | | |
|---|---|---|---|
| 2,681,346 A | * 6/1954 | France | 540/121 |
| 2,850,505 A | * 9/1958 | Hein | 540/121 |
| 2,951,798 A | * 9/1960 | Sharp | 204/157.6 |
| 4,814,256 A | * 3/1989 | Aldag et al. | 430/270.16 |
| 4,846,551 A | 7/1989 | Rancourt et al. | |
| 2003/0156080 A1 | * 8/2003 | Koike et al. | 345/60 |

FOREIGN PATENT DOCUMENTS

| | | |
|---|---|---|
| JP | 62-258402 A | 11/1987 |
| JP | 02-39161 A | 2/1990 |
| JP | 02-296885 A | 12/1990 |
| JP | 11-116574 A * | 4/1999 |
| JP | 2000-191948 A * | 7/2000 |
| JP | 2001-220551 A * | 8/2001 |

* cited by examiner

SELECTIVELY LIGHT-ABSORPTIVE MATERIAL, COATING COMPOSITION CONTAINING THE SAME, AND FILTER MANUFACTURED USING THE COATING COMPOSITION FOR COLOR DISPLAYS

TECHNICAL FIELD

The present invention relates to a selectively light-absorptive material, a coating composition containing the material, and a filter manufactured using the coating composition, which are for use in color displays with enhanced color purity and contrast.

BACKGROUND ART

Color displays have been extensively applied to television, computer monitors, video game machines and the like. Cathode ray tubes (CRTs), which are a kind of display adopted for almost all of these applications, are based on the principle of energy conversion, i.e., from motion energy to light energy, in which electrons emitted from an electron gun hit phosphors of a screen and excites the phosphors. Since light emitted from the phosphors belongs to the visible range, CRTs can be used for displays such as common televisions or computer monitors. CRTs are able to display the full range of colors with the three principal colors: red (R), green (G) and blue (B).

FIGS. 1 and 2 show the emission spectra for CRTs and plasma display panels (PDPs), respectively. As shown in FIGS. 1 and 2, a considerable amount of light is emitted from the peripheral region adjacent to the three main R, G and B peaks, so that color purity is deteriorated and color reproduction range is limited. FIG. 1 shows the typical emission spectrum of a CRT. As shown in FIG. 1, typically a green-color emission spectrum is wide and tends to be close to the yellow range. Thus, as for CRTs, red and blue color emission can be achieved with high-color purity. However, as for green color emission, yellowish green light, rather than pure green light, is emitted.

On the other hand, reflection of ambient light from the surface of a display causes eye strain to viewers, and degrades the contrast of the display when the display is exposed to bright ambient light. Reflection of light, which occurs in displays, involves the reflection of ambient light from a screen, for example, a glass panel, and from phosphors arranged inside the screen. To reduce such reflection of light, research has been conducted. For example, U.S. Pat. No. 4,989,953 relates to a reduction of reflected light. However, this disclosure is limited only to reducing glare caused by reflection of external light in a monochromic monitor.

As a trial for reducing the reflection of light in color displays, a neutral density (ND) filter or an attenuator has been adopted. The ND filter, which is manufactured by coating an appropriate medium with a silver or graphite colloid suspension and attaching the medium to the surface of the monitor, improves contrast by transmitting only a portion of light regardless of the wavelength. However, the ND filter lowers brightness.

As another technique for reducing the reflection of light in color displays, an antireflection coating may accompany the ND filter. This combination technique can decrease the reflection of ambient light from phosphors, and the reflection of light from the surface of the display panel. This method is unsuitable for improving the brightness and color purity.

To improve both color purity and contrast, and to minimize a reduction in brightness, a method of transmitting only light of three principal color regions and blocking light of the other regions has been suggested. Compared to the ND filter, this method is able to block ambient light and fully transmit light generated in a display, and thus the reduction in brightness can be minimized with increased contrast. In addition, various colors other than the three principal colors, which are generated in the display, are effectively blocked, thereby improving color purity and expanding color reproduction range.

U.S. Pat. Nos. 4,288,250, 4,520,115 and 4,245,242 teach the use of a colored glass as a material for the front panel of a display, or as a filter, which contains a metal oxide including neodymium oxide. These disclosures allow the passage of light of the three principal color range emitted in the display and limit the transmission of light outside this range, so that a reduction in brightness is prevented and reflectivity of ambient light is lowered with improved color purity. However, the manufacture of the colored glass is complicated and the manufacturing cost increases. Thus, the methods are economically unfavorable.

JP Publication No. sho 44-5091, and JP Laid-open Publication Nos. sho 59-217705, hei 4-106150, hei 6-88007 and hei 10-120860 disclose the improvement in display properties of a color display using a colored plastic manufactured by dispersing or dissolving a neodymium oxide or an organic neodymium compound in plastic resin. However, there are difficulties in the dispersing or dissolving process of these methods. Furthermore, the plastic material changes into a yellowish color and the display properties gradually deteriorate with time.

JP Laid-open Publication No. hei 2-210480 and U.S. Pat. No. 5,200,667 suggest a filter for color displays, which contains a pigment and a plastic resin material as major components. However, the pigment suggested by the disclosures has a wide absorption bandwidth and a low light selectivity. Thus, the color purity cannot be improved. U.S. Pat. No. 5,834,122 discloses a band pass filter for displays with improved light selectivity, which contains a highly color-selective pigment. However, because pigments absorbing light in the range between green and red colors and light in the range between blue and green colors have weak durability, the method is unpractical.

Use of another type of display, the plasma display panels (PDPs), is gradually increasing. As for PDPs, a space enclosed by barrier walls made of glass is filled with inert gases including helium (He), neon (Ne), argon (Ar) or xenon (Xe), or a mixture of these gases, and the gases filling the space are ionized to create plasma by applying a high voltage. At this time, ultraviolet (UV) rays are emitted to excite phosphors. PDPs provide a wider viewing angle, and are easier to enlarge compared to other displays. Thus, PDPs as a thin-type luminescent display have been considered as highly potential display devices for high-definition televisions.

Now, such PDPs are under development by many display manufacturers. However, their brightness is low and the reflection of light from the surface of the phosphor is serious. Furthermore, the filling gas, He, emits light with an orange color, and thus the color purity is poor compared to CRTs.

FIG. 2 shows the emission spectrum of PDPs. Compared to the emission spectrum of CRTs shown in FIG. 1, the emission peak of green tends to have a slightly shorter wavelength, and the emission peak of blue tends to have a longer wavelength. Also, a strong emission peak of red is shown near 590 nm. This emission peak of red near 590 nm originates from the use of Ne as an inert gas. Thus, it is difficult to display pure red color. As for blue color, greenish blue light, rather than pure blue light, is displayed.

In terms of various uses of CRTs and PDPs and potential uses thereof, there is a need for an apparatus and mechanism capable of lowering the reflection from the surface of a display, and improving color purity and contrast without considerable loss in brightness and distinctness.

To satisfy these requirements, the present inventors have actively carried out research so as to improve the color purity and contrast by absorbing light reflection in a color display. As a result, it has been found that use of a light absorbing material capable of absorbing light between the green and UV regions, between the green and red regions, and between the red and infrared regions, from the emission spectrum, as a filter for color displays, can improve color purity and contrast in the color display.

DISCLOSURE OF THE INVENTION

A first object of the present invention is to provide a selectively light-absorptive material for color displays, which is able to absorb light reflected in a color display and light of the intermediate colors exclusive of the three principal colors, with improved color purity and contrast in the color display.

A second object of the present invention is to provide a selectively light-absorptive coating composition containing the light-absorptive material.

A third object of the present invention is to provide a selectively light-absorptive filter including the selectively light-absorptive material.

The first object of the present invention is achieved by a selectively light-absorptive material for a color display, comprising a tetrazaporphyrine derivative having formula (1)

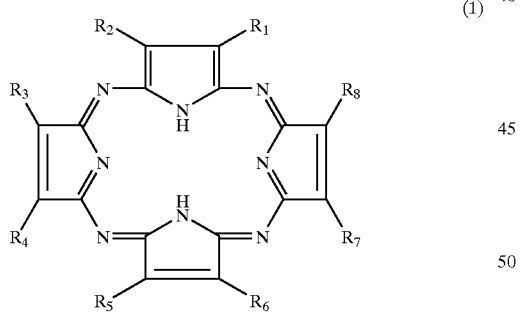

(1)

where $R_1$, $R_2$, $R_3$, $R_4$, $R_5$, $R_6$, $R_7$ and $R_8$ are independently selected from the group consisting of hydrogen; an unsubstituted phenyl group, an alkyl group of 1 to 8 carbon atoms; an alkoxy group of 1 to 8 carbon atoms; a nitro group; halogen atoms; a halide; a cyano group; an alkylamino group of 1 to 8 carbon atoms; an aminoalkyl group of 1 to 8 carbon atoms; and a phenyl group having a substitutent selected from an alkyl group of 1 to 8 carbon atoms, an alkoxy group of 1 to 8 carbon atoms, a nitro group, halogen atoms, a halide, an alkylamino group of 1 to 8 carbon atoms, an aminoalkyl group of 1 to 8 carbon atoms and a cyano group, or two neighboring substituents among $R_1$, $R_2$, $R_3$, $R_4$, $R_5$, $R_6$, $R_7$ and $R_8$ are fused and substituted with 1 to 3 aromatic cyclic compounds having formula (2a) through (2g), and unsubstituted groups among $R_1$, $R_2$, $R_3$, $R_4$, $R_5$, $R_6$, $R_7$ and $R_8$ are independently selected from the group consisting of hydrogen, an alkyl group of 1 to 8 carbon atoms, an alkoxy group of 1 to 8 carbon atoms, an allyl group, halogen atoms, a halide, a cyano group and a nitro group

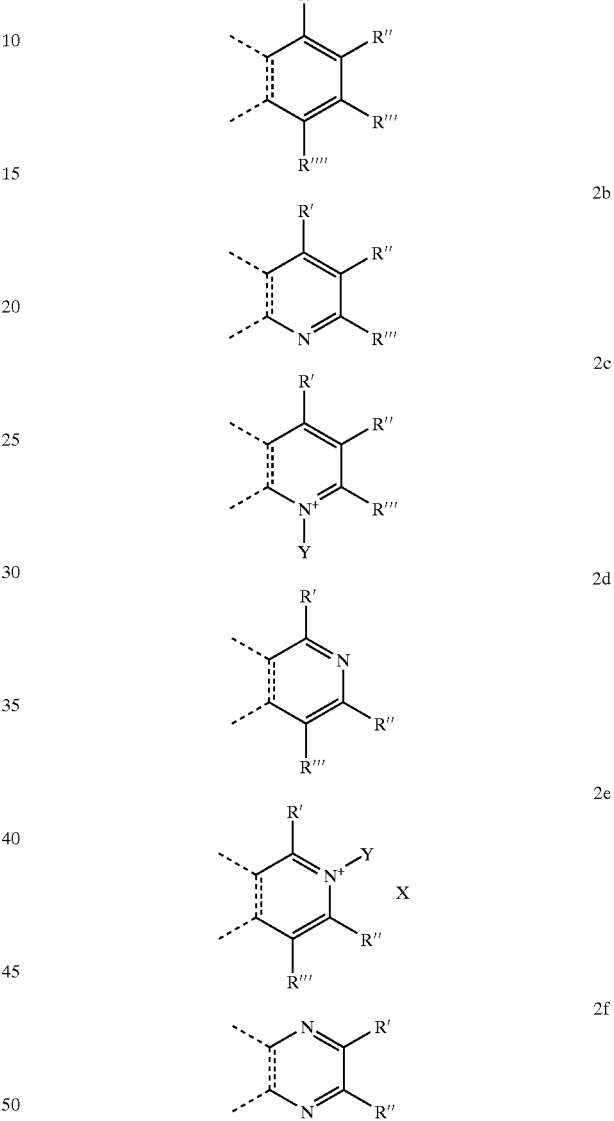

where R', R", R"' and R"" are independently selected from the group consisting of hydrogen, an alkyl group of 1 to 8 carbon atoms, an alkoxy group of 1 to 8 carbon atoms, an allyl group, a cyano group and a nitro group; X is halogen atoms or alkyl sulfonate of 1 to 8 carbon atoms; Y is an alkyl or allyl group of 1 to 8 carbon atoms; and dashed lines indicate a portion coupled with the pyrrole group of formula (1).

In another embodiment, a selectively-light absorptive material for a color display, may comprise a tetrazaporphyrine derivative having formula (3)

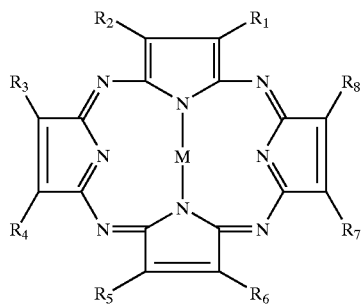

(3)

where $R_1$, $R_2$, $R_3$, $R_4$, $R_5$, $R_6$, $R_7$ and $R_8$ are independently selected from the group consisting of hydrogen; an unsubstituted phenyl group, an alkyl group of 1 to 8 carbon atoms; an alkoxy group of 1 to 8 carbon atoms; a nitro group; halogen atoms; a halide; a cyano group; an alkylamino group of 1 to 8 carbon atoms; an aminoalkyl group of 1 to 8 carbon atoms; and a phenyl group having a substitute group selected from an alkyl group of 1 to 8 carbon atoms, an alkoxy group of 1 to 8 carbon atoms, a nitro group, halogen atoms, a halide, an alkylamino group of 1 to 8 carbon atoms, an aminoalkyl group of 1 to 8 carbon atoms and cyano groups, or two neighboring substituents among $R_1$, $R_2$, $R_3$, $R_4$, $R_5$, $R_6$, $R_7$ and $R_8$ are fused and substituted with 1 to 3 aromatic cyclic compounds having formula (2a) through (2g), and unsubstituted groups among $R_1$, $R_2$, $R_3$, $R_4$, $R_5$, $R_6$, $R_7$ and $R_8$ are independently selected from the group consisting of hydrogen, an alkyl group of 1 to 8 carbon atoms, an alkoxy group of 1 to 8 carbon atoms, an allyl group, halogen atoms, a halide, a cyano group and a nitro group;

M is metal ions with an oxidation number of 2 capable of being complexed with the tetrazaporphyrine ring, or metal ions having ligands with an oxidation number of 2 capable of being complexed with the tetrazaporphyrine rings

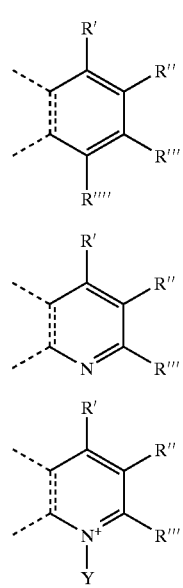

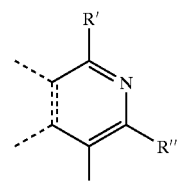

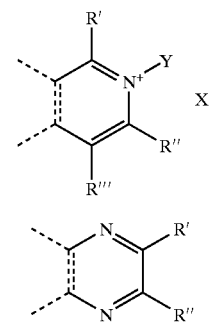

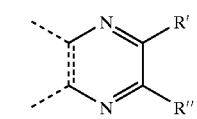

where R', R", R'" and R"" are independently selected from the group consisting of hydrogen, an alkyl group of 1 to 8 carbon atoms, an alkoxy group of 1 to 8 carbon atoms, an allyl group, a cyano group and a nitro group; X is halogen atoms or alkyl sulfonate of 1 to 8 carbon atoms; Y is an alkyl or allyl group of 1 to 8 carbon atoms; and dashed lines indicate a portion coupled with the pyrrole group of formula (3).

The second object of the present invention is achieved by a selectively light-absorptive coating composition comprising the light-absorptive material, a plastic resin and an organic solvent.

The third object of the present invention is achieved by a selectively light-absorptive filter for a color display, formed of the selectively light-absorbing material and a plastic resin.

BEST MODE FOR CARRYING OUT THE INVENTION

Figure 1:
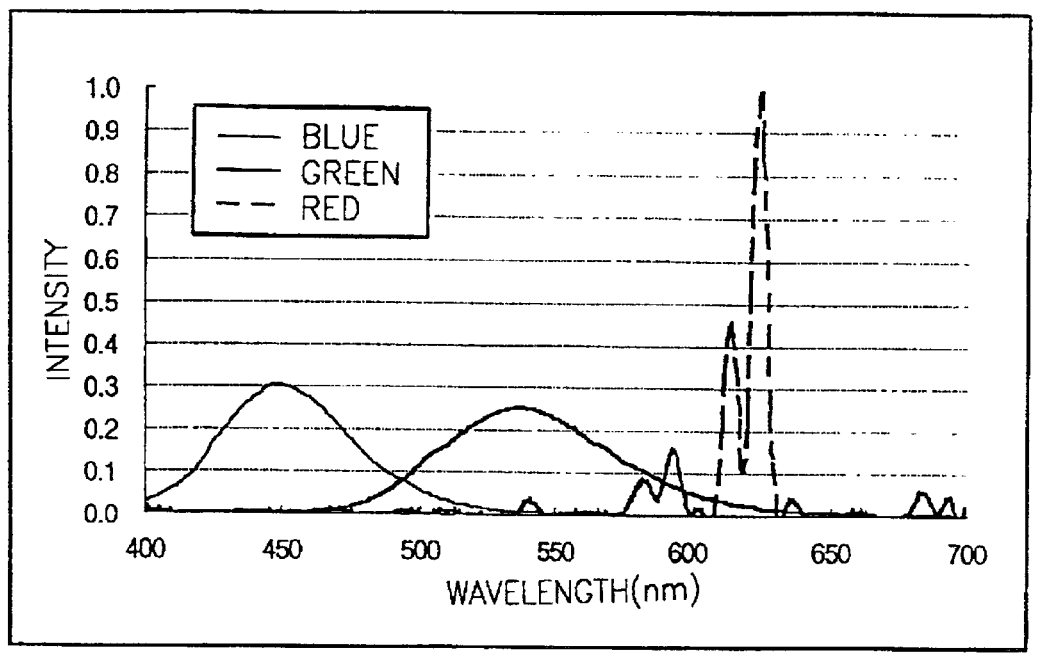
FIG. 1 is a typical emission spectrum of cathode ray tubes (CRTs)
Figure 2:
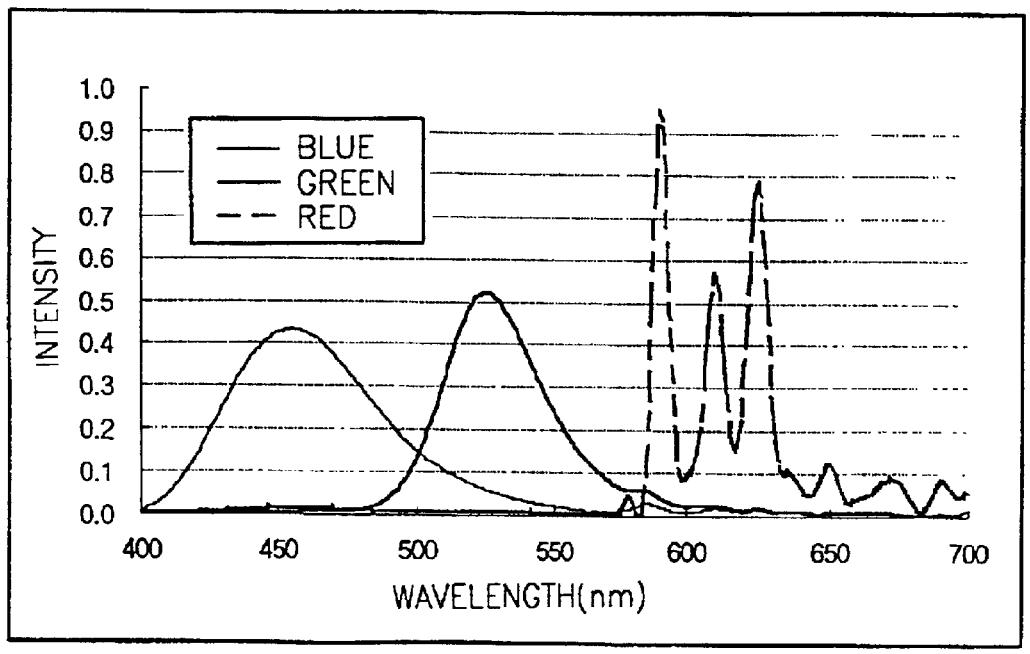
FIG. 2 is a typical emission spectrum of plasma display panels (PDPs)

To improve color purity and contrast in color displays, there is a need for a selectively light-absorptive material capable of absorbing light between the green and ultraviolet (UV) regions, between the blue and green regions, between the green and red regions, and between the red and infrared regions. In particular, ideal light-absorptive materials capable of absorbing light between the blue and green regions, and between the green and red regions need the following requirements.

(1) The Light-Absorptive Material for the Region Between the Blue and Green Regions Maximum absorption wavelength: 460 to 500 nm Absorption bandwidth: 20 to 30 nm (2) The Light-Absorptive Material for the Region Between the Green and Red Regions Maximum absorption wavelength: 550 to 600 nm Absorption bandwidth: 50 to 70 nm The tetazaporphyrine derivative having formula (1) hereinabove according to the present invention have a primary absorption band in the region between 530 to 620 nm, and a secondary absorption band in the region between 620 to 700 nm. Each of the absorption bands in the two regions has a width of about 30 to 50 nm. The tetrazaporphyrine derivatives having formula (3) hereinabove have a primary absorption band in the region between 570 and 610 nm with a width of about 30 to 50 nm. Thus, the tetrazaporphyrine derivatives having formulae (1) and (3) according to the present invention have excellent selective light absorbency in the region between the green and red regions, which is required for an optical filter for color displays.

The tetrazaporphyrine derivatives having formulae (1) and (3) selectively absorb light between the green and red regions, thereby sharply improving color purity and contrast in color displays. In addition, the tetrazaporphyrine derivatives having formula (1) and (3) exhibit excellent heat resistance and light resistance, so that application of these derivatives to image display displays, such as cathode ray tubes (CRTs) or plasma displays (PDPs), ensures that the displays have a long lifespan.

As for $R_1$, $R_2$, $R_3$, $R_4$, $R_5$, $R_6$, $R_7$ and $R_8$ of the tetrazaporphyrine derivative having formula (1) or (3), the alkyl group of 1 to 8 carbon atoms may include methyl, ethyl, propyl, butyl, isobutyl, t-butyl, pentyl, isopentyl, neopentyl and octyl groups, and the alkoxy group of 1 to 8 carbon atoms may include methoxy, ethoxy, propoxyl, butoxyl and pentoxyl groups. The halogen atom may include fluorine (F), chlorine (Cl), iodine (I) and bromine (Br), and the halide may include chloromethyl, bromomethyl, iodomethyl and fluoromethyl groups. The alkylamino group of 1 to 8 carbon atoms may include methylamino and ethylamino groups, and the aminoalkyl group of 1 to 8 carbon atoms may include aminomethyl and aminoethyl groups.

In the tetrazaporphyrine derivative having formula (1) or (3), two neighboring substituents among $R_1$, $R_2$, $R_3$, $R_4$, $R_5$, $R_6$, $R_7$ and $R_8$ may fused with each other, resulting in 2 to 3 cyclic compounds having formula (2a). Preferably, in the cyclic compound having formula (2a), at least one of R', R", R'" and R"" is an alkyl group of 2 to 6 carbon atoms or an alkoxy group of 2 to 6 carbon atoms.

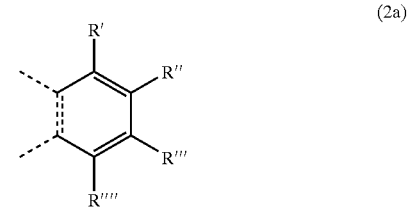

(2a)

Preferably, in the tetrazaporphyrine derivative, $R_1$, $R_2$, $R_3$, $R_4$, $R_5$, $R_6$, $R_7$ and $R_8$ are independently selected from an unsubstituted phenyl group, or a substituted phenyl group having 1 to 5 substituents selected from the group consisting of an alkyl group of 1 to 8 carbon atoms, an alkoxy group of 1 to 8 carbon atoms, a nitro group, halogen atoms, an alkylamine group of 1 to 8 carbon atoms, an aminoalkyl group of 1 to 8 carbon atoms, and a cyano group.

Preferably, the tetrazaporphyrine derivative having formula (1) is selected from the compounds having the following formulae.

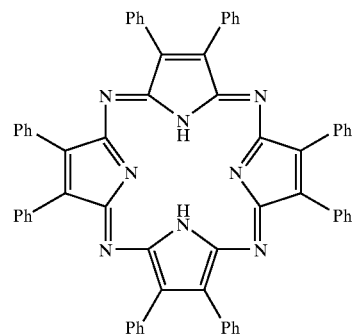

-continued
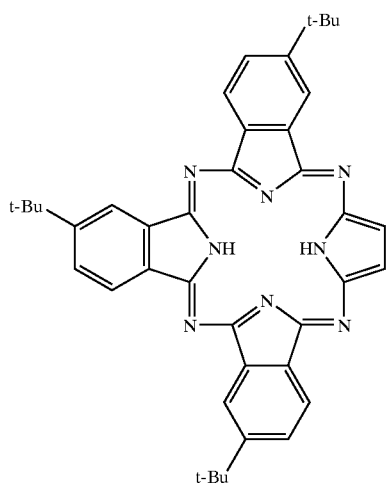
In the tetrazaporphyrine derivative having formula (3), M is Ni, Mg, Mn, Co, Cu, Ru or V, or Mn or Ru coordinated with at least one ligand selected from ammonia, water and halogen atoms. Preferably, the tetrazaporphyrine derivative having formula (3) is selected from the compounds having the following formulae.
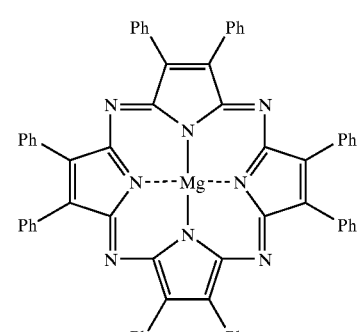
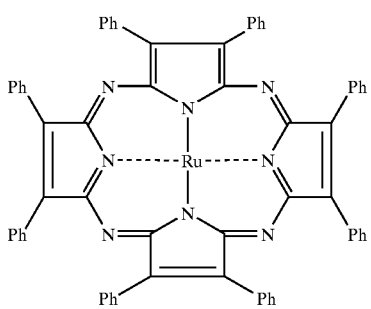
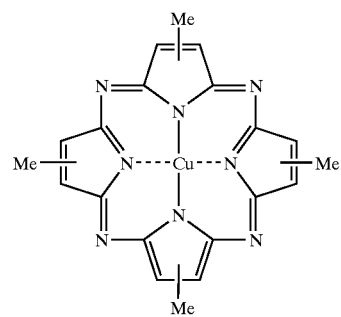
-continued
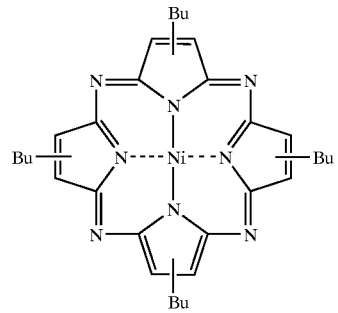
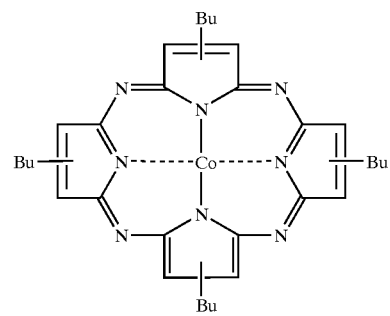
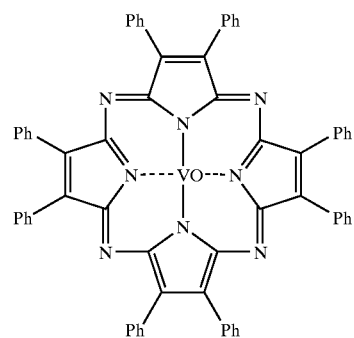
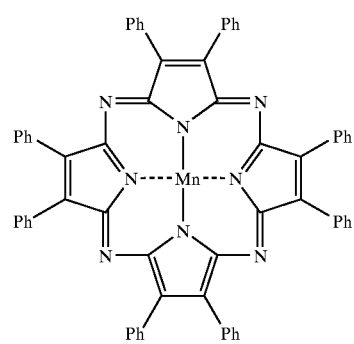
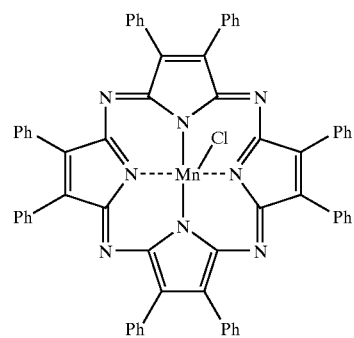

-continued

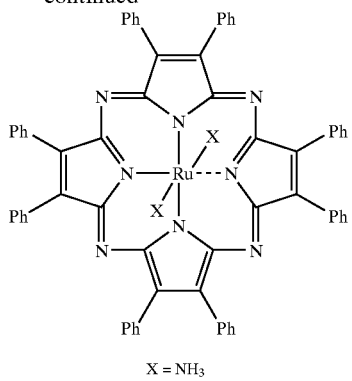

X = NH₃

From the selectively light-absorptive material according to the present invention, a coating composition can be obtained by dissolving the selectively light-absorptive material in an organic solvent along with a plastic resin. The amount of the selectively light-absorptive material is in the range of 0.05–1% by weight based on the solid content of the coating composition. If the content of the selectively light-absorptive material is less than 0.05% by weight, the absorption characteristics are insufficient. If the content of the selectively light-absorptive material exceeds 1% by weight, the physical properties of the coating composition are unfavorable.

For the selectively light-absorptive coating composition, the plastic resin may be a transparent plastic resin such as poly(methylmethacrylate), polyvinyl alcohol, polycarbonate, ethylene vinylacetate and polyvinylbutyral. The amount of the transparent plastic resin may be in the range of 5–40% based on the total weight of the organic solvent. If the content of the is transparent plastic resin is less than 5% by weight, it is difficult to ensure a thickness sufficient for the required physical properties. If the content of the transparent plastic resin exceeds 40% by weight, the coating characteristics deteriorate.

The organic solvent may include toluene, xylene, propylalcohol, isopropylalcohol, methylcellosolve, ethylcellosolve and dimethylformamide.

To adjust the transmittance of a color display device for each wavelength region, or provide whiteness, the selectively light-absorptive coating material may further comprise a common azo dye, cyanine dye, diphenylmethane dye, triphenylmethane dye, phthalocyanine dye, xanthane series dye, diphenylene series dye, indigo dye and porphyrine dye. Preferably, The amount of dye is in the range of 0.05–3% by weight based on the total solid content of the coating composition. If the amount of dye is less than 0.05% by weight, the absorption characteristics are insufficient. If the amount of dye exceed 3% by weight, the physical properties of the coating composition are unfavorable.

Preferably, the coating composition according to the present invention further comprises an infrared ray blocking agent so as to block infrared rays (particularly, near infrared rays) reflected from a color display, and particularly, from a plasma display panel. The infrared ray blocking agent may include the compounds having formulae (4), (5) and (6).

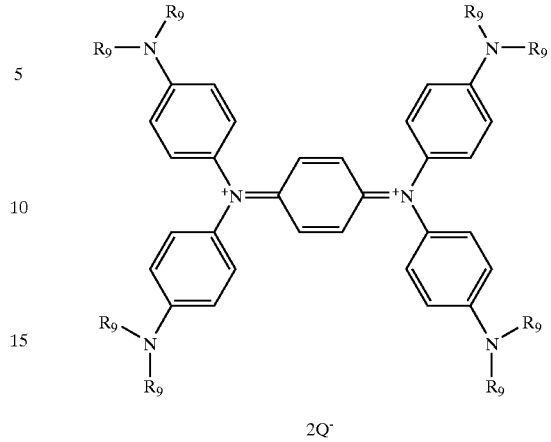

2Q⁻

In formula (4), $R_9$ is an alkyl group of 1 to 6 carbon atoms, and Q is $ClO_4$, $Ab_2F_6$, $BF_3$, toluene sulfonate or benzene sulfonate.

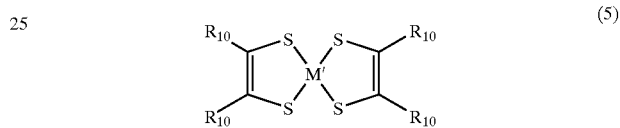

In formula (5), M is nickel (Ni), palladium (Pd) or platinum (Pt), $R_{10}$ is hydrogen, an alkyl group of 1 to 10 carbon atoms, an alkoxy group of 1 to 10 carbon atoms, a substituted phenyl group with halogen atom or alkylamine, or an unsubstituted phenyl group.

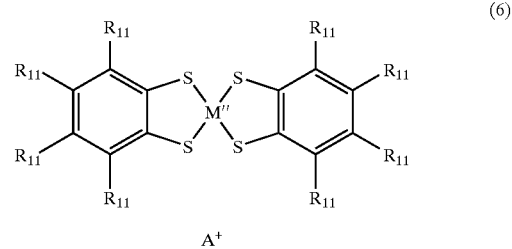

A⁺

In formula (6), M" is iron (Fe), Ni, copper (Cu), cobalt (Co) or Pt; $R_{11}$ is hydrogen, an alkyl group of 1 to 10 carbon atoms, an alkoxy group of 1 to 10 carbon atoms, halogen atoms, or a nitro group; and A⁺ indicates the positive ions of tetraalkylammonium, wherein the alkyl group has 1 to 6 carbon atoms.

To enhance light resistance, the selectively light-absorptive coating composition according to the present invention may further include a stabilizer. Potential stabilizers may be a radical reaction inhibitor, which prevents discoloration of pigments.

The selectively light-absorptive coating composition according to the present invention may be coated on glass or a plastic film, which is then mounted on a display, or directly coated on the surface of a display. This coating process may be carried out using a common technique, such as spin coating or roll coating. Preferably, the selectively light-absorptive coating composition is coated to a thickness of 1–20 μm. If the thickness of the coated layer is less than 1 μm, the absorption characteristics are insufficient. If the thickness of the coated layer exceeds 20 μm, the coating characteristics deteriorate.

The selectively light-absorptive filter according to the present invention is obtained by coating the coating composition as previously described, and drying the coated layer. During the drying process, the solvent is completely removed from the coating composition, and thus the resultant selectively light-absorptive filter contains only the tetrazaporphyrazine derivative having formula (1) or (3), and the plastic resin.

Hereinafter, the present invention will be described by way of examples. However, these examples are merely illustrative and not intended to limit the scope of the invention.

SYNTHESIS EXAMPLE 1

Octaphenyl Tetrazaporphyrine

Octaphenyl tetrazaporphyrine having formula (1) or (3), wherein $R_1, R_2, R_3, R_4, R_5, R_6, R_7$ and $R_8$ are phenyl groups, was synthesized as follows by the method disclosed in *J. Am. Soc.*, 929 (1937).

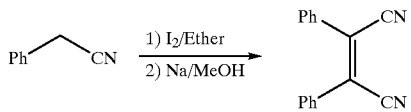

100 parts by weight of iodine, 50 parts by weight of phenylacetonitrile and 1500 parts by weight of ethylether were placed in a three-neck round bottomed flask, and completely mixed and dissolved. 300 parts by weight of a methanol solution containing 18% by weight of sodium, which had been cooled with iced water, were slowly added to the mixture for 30 minutes.

After the reaction was completed, water, a diluted thiosulfuric acid solution, water and a sodium sulfate solution were consecutively added to the is reaction mixture. Next, the solvent was removed and the resulting yellow solid product was vacuum distilled to obtain diphenylmaleinitrile with a yield of 50%.

5 parts by weight of the diphenylmaleinitrile and 0.5 parts by weight magnesium (Mg) were reacted at 275° C. for 10 minutes to produce violet crystals. The remaining metal was removed using a diluted acetic acid. A sodium carbonate solution was added to the resulting product, and heated to 50° C. to hydrolyze the unreacted nitrile compound. The resulting magnesium octaphenyl porphyrazine was washed with excess hot water, and dried.

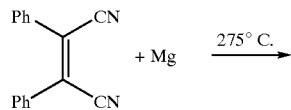

Figure 3:
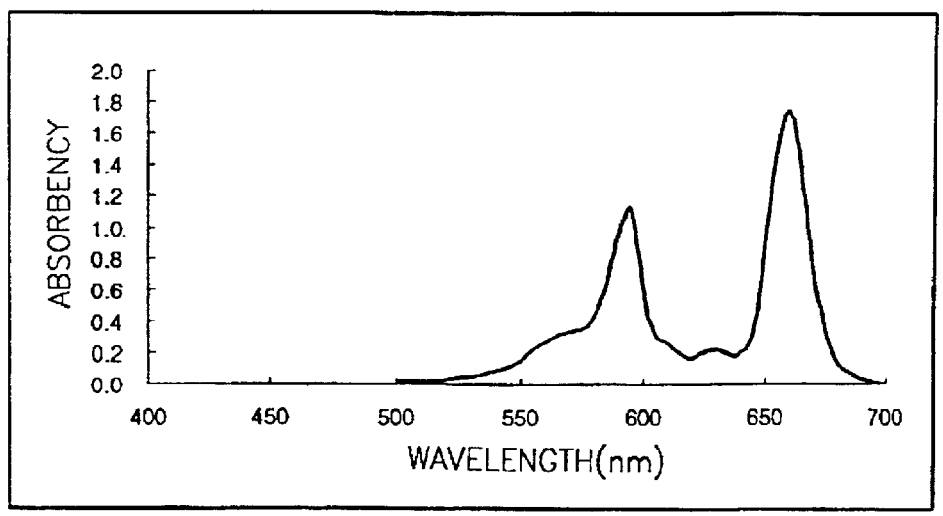
FIG. 3 is the absorption spectrum of octaphenyl tetrazaporphyrine, which was obtained as a selectively light-absorptive material in Synthesis Example 1 according to the present invention.

The magnesium octaphenyl porphyrazine was put in a diluted hydrochloric acid solution and heated until magnesium ions were separated from the compound. The resulting product was dissolved and recrystalized in benzene to obtain octaphenyl tetrazaporphyrine. The absorption spectrum of the octaphenyl tetrazaporphyrine is shown in FIG. 3.

SYNTHESIS EXAMPLE 2

Tribenzyl Tetrazaporphyrine

Tribenzyl tetrazaporphyrine having formula (1) or (3), wherein $R_2$ is a t-butyl group, and $R_1, R_3, R_4, R_5, R_6, R_7$ and $R_8$ are hydrogen, was synthesized as follows, by the method disclosed in *J. Am. Soc.*, 112, 9641 (1990).

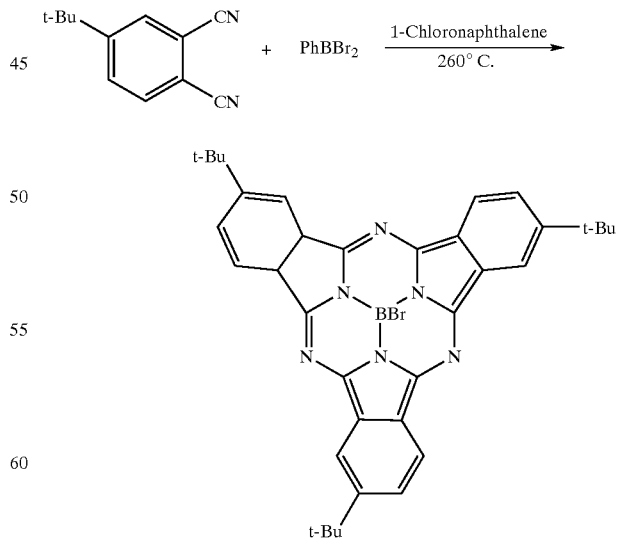

30 g of 1-chloronaphthalene, 10 g of t-butylphthalonitrile and 10 g of phenyldibromoborane were placed in a three-neck round bottomed flask, and heated and melted at 260° C.

for about 10 minutes for reaction, so that tributylated sub-phthalocyanine was obtained with a yield of 50%.

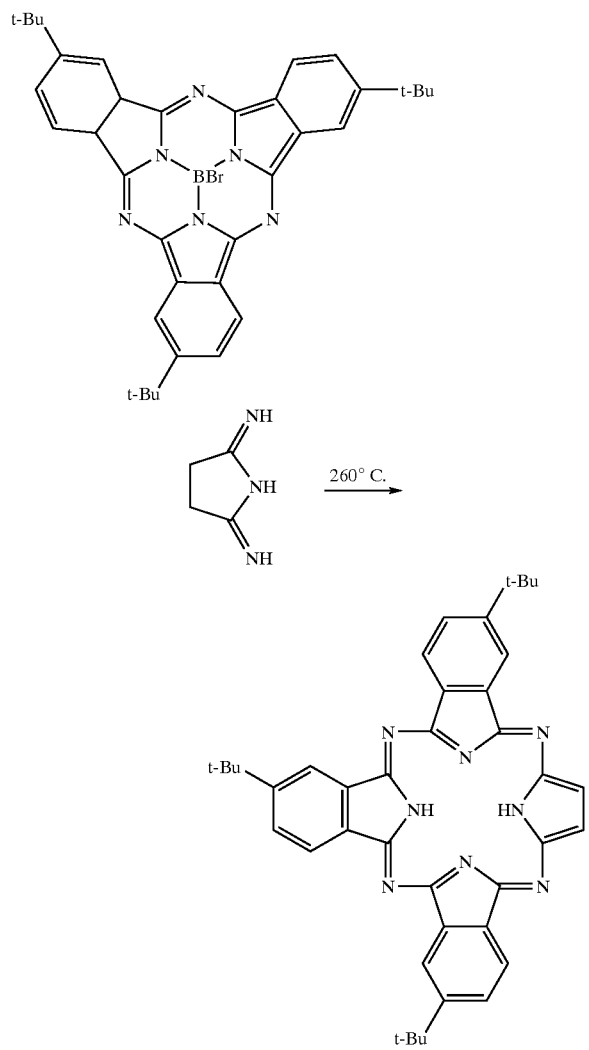

Figure 4:
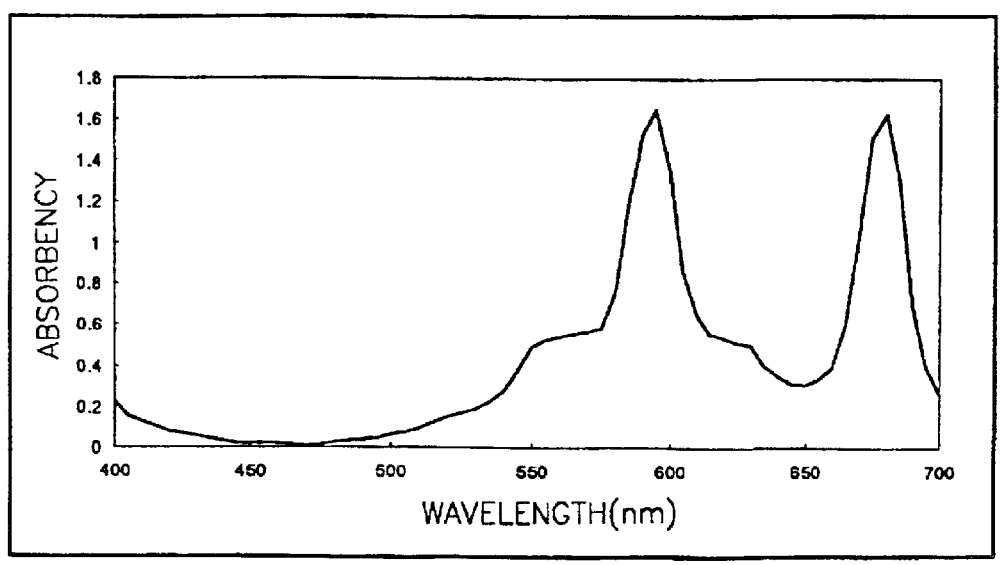
FIG. 4 is the absorption spectrum of tribenzyl tetrazaporphyrine, which was obtained as a selectively light-absorptive material in Synthesis Example 2 according to the present invention.

1 equivalent of the tributylated sub-phthalocyanine, and 1 equivalent of diiminoisoindoline was dissolved in a mixture of dimethylsulfoxide and 1-chloronaphthalene (a ratio of 2:1 by volume), and reacted at 80 to 90° C. for 24 hours. The resulting product was evaporated under reduced pressure to remove the solvent, and purified by chromatography to obtain light blue tribenzyl tetrazaporphyrine in the form of powder. The absorption spectrum of the tribenzyl tetrazaporphyrine is shown in FIG. 4.

SYNTHESIS EXAMPLE 3

Ruthenium Octaphenyl Tetrazaporphyrazine

Ruthenium octaphenyl tetrazaporphyrazine was synthesized as follows by the method disclosed in *J. Am. Soc.,* 929 (1937).

100 parts by weight of iodine, 50 parts by weight of phenylacetonitrile and 1500 parts by weight of ethylether were placed in a three-neck round bottomed flask, and completely mixed and dissolved. 300 parts by weight a methanol solution containing 18% by weight of sodium, which had been cooled with iced water, were slowly added to the mixture for 30 minutes.

After the reaction was completed, water, a diluted thiosulfuric acid solution, water and a sodium sulfate solution were consecutively added to the reaction mixture. Next, the solvent was removed and the resulting yellow solid product was vacuum distilled to obtain diphenylmaleinitrile with a yield of 50%.

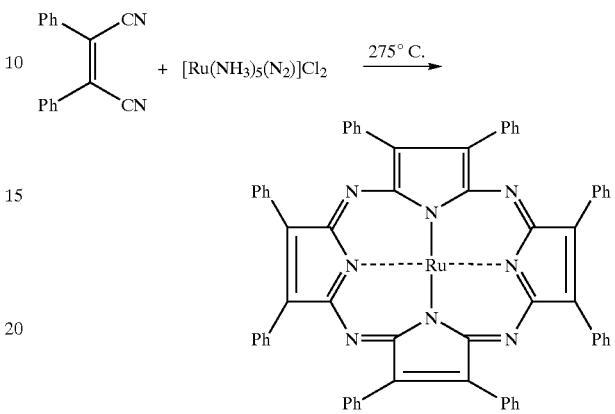

Figure 5:
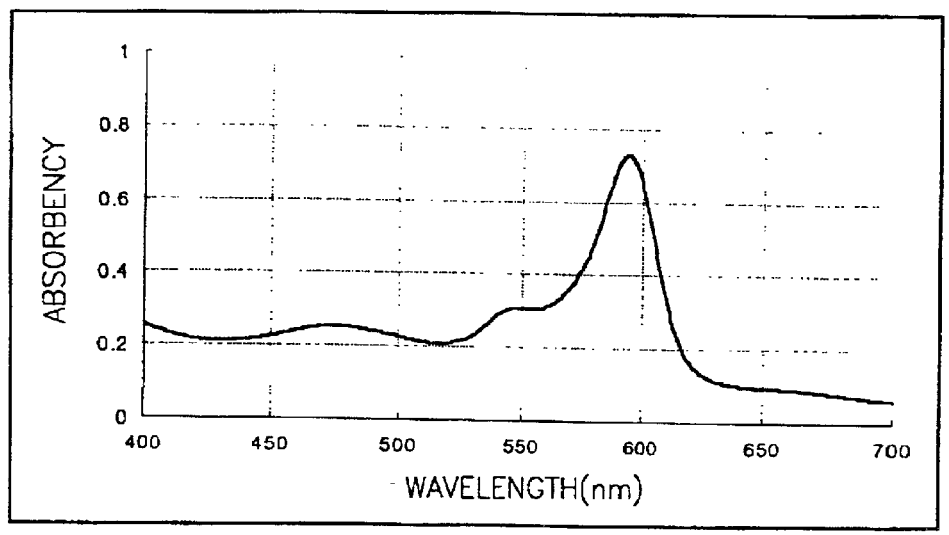
FIG. 5 is the absorption spectrum of ruthenium (Ru) octaphenyl tetrazaporphyrazine, which was obtained as a selectively light-absorptive material in Synthesis Example 3 according to the present invention.

5 parts by weight of the diphenylmalenitrile and 0.5 parts by weight pentaaminedinitrozen ruthenium dichloride ([Ru(NH$_3$)$_5$(N$_2$)]Cl$_2$) were reacted at 275° C. for 30 minutes to produce violet crystals. The remaining metal was removed using a diluted acetic acid. A sodium carbonate solution was added to the resulting product, and heated to 50° C. to hydrolyze the unreacted nitrile compound. The resulting ruthenium octaphenyl tetrazaporphyrazine was washed with excess hot water, and dried. The absorption spectrum of the ruthenium octaphenyl tetrazaporphyrazine is shown in FIG. 5.

SYNTHESIS EXAMPLE 4

Copper Tetramethyl Tetrazaporphyrazine

Copper tetramethyl tetrazaporphyrazine was synthesized as follows by the method disclosed in *J. Am. Soc.,* 4839 (1952).

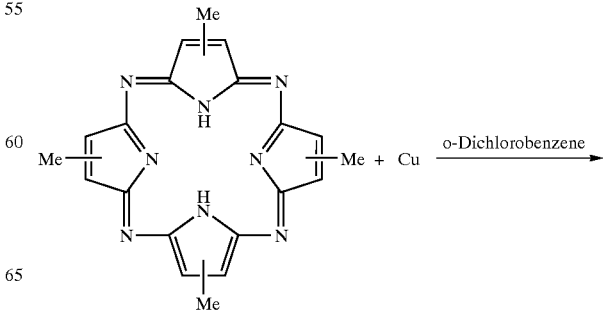

-continued

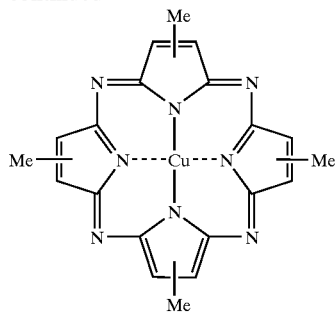

Figure 6:
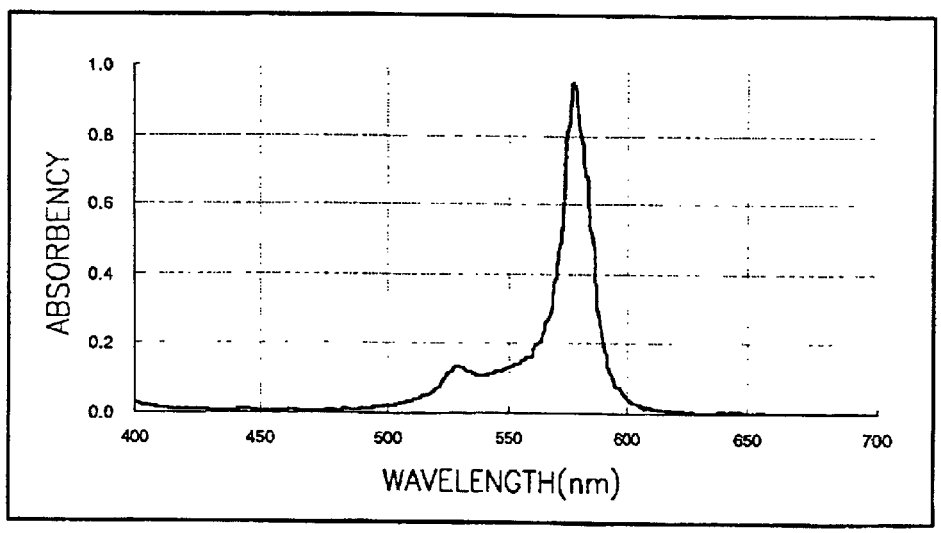
FIG. 6 is the absorption spectrum of copper tetramethyl tetrazaporphyrazine, which was obtained as a selectively light-absorptive material in Synthesis Example 4 according to the present invention.

60 parts by weight of metal-free tetramethyl tetrazaporphyrine and 1.5 parts by weight of anhydrous copper were refluxed for 3 hours in 25 parts by weight of o-dichlorobenzene. After the reaction was completed, the reaction mixture was cooled and filtered. The resulting product was extracted using chloroform, and crystalized to obtain pure copper tetramethyl tetrazaporphyrazine with a yield of 33%. The absorption spectrum of the copper tetramethyl tetrazaporphyrazine is shown in FIG. 6.

SYNTHESIS EXAMPLE 5

Nickel Tetrabutyl Tetrazaporphyrazine

Nickel tetrabutyl tetrazaporphyrazine was synthesized as follows by the method disclosed in J. Am. Soc., 4839 (1952).

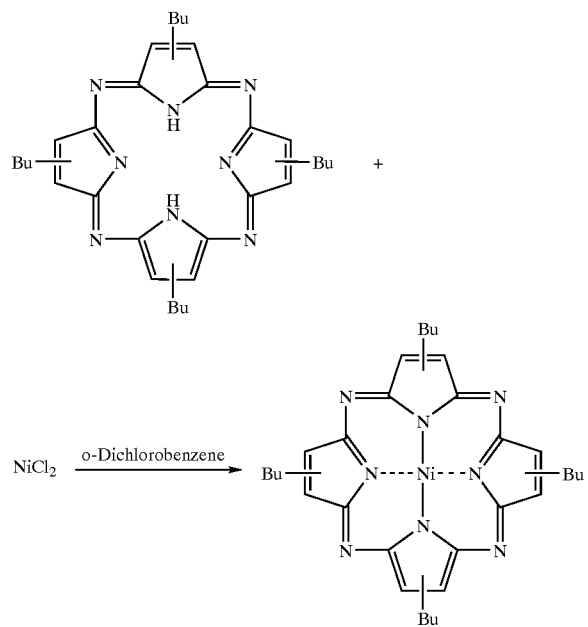

Figure 7:
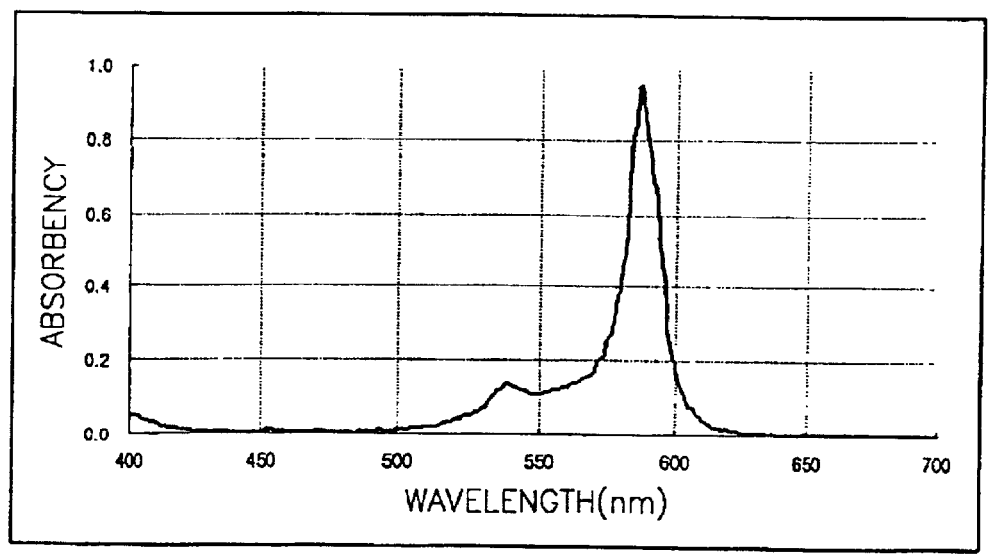
FIG. 7 is the absorption spectrum of nickel tetrabutyl tetrazaporphyrazine, which was obtained as a selectively light-absorptive material in Synthesis Example 5 according to the present invention.

50 parts by weight of metal-free tetrabutyl tetrazaporphyrine and 1.5 parts by weight of anhydrous nickel chloride were refluxed for 1.5 hours in 25 parts by weight of o-dichlorobenzene. After the reaction was completed, the hot reaction mixture was filtered before the reaction mixture was cooled. The resulting solid product was washed with hot water and ethanol, and then extracted using chlorobenzene. Next, the resulting product was crystalized to obtain pure nickel tetrabutyl tetrazaporphyrazine. The absorption spectrum of the nickel tetrabutyl tetrazaporphyrazine is shown in FIG. 7.

SYNTHESIS EXAMPLE 6

Cobalt Tetrabutyl Tetrazaporphyrazine

Cobalt tetrabutyl tetrazaporphyrazine was synthesized as follows by the method disclosed in J. Am. Soc., 4839 (1952).

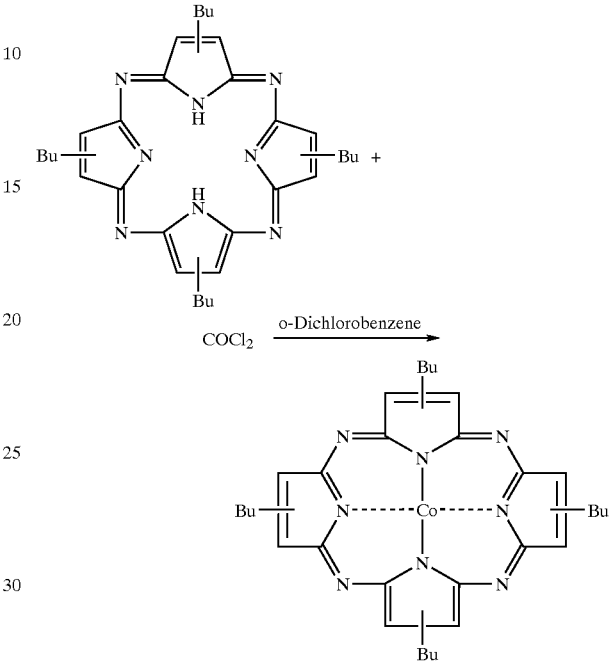

50 parts by weight of metal-free tetrabutyl tetrazaporphyrine and 1.5 parts by weight of anhydrous cobalt chloride wee refluxed for 1.5 hours in 25 parts by weight of o-dichlorobenzene. After the reaction was completed, the hot reaction mixture was filtered before the reaction mixture was cooled. The resulting solid product was washed with hot water and ethanol, and then extracted using chlorobenzene. Next, the resulting product was crystalized to obtain pure cobalt tetrabutyl tetrazaporphyrazine.

SYNTHESIS EXAMPLE 7

Vanadium Oxide Octaphenyl Tetrazaporphyrazine

Vanadium oxide octaphenyl tetrazaporphyrazine was synthesized as follows by the method disclosed in J. Am. Soc., 4839 (1952).

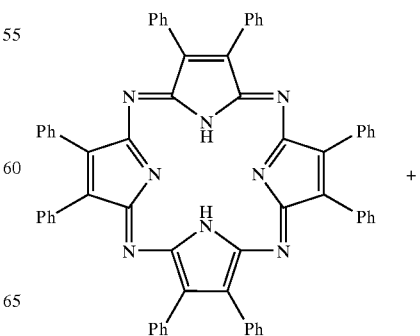

-continued

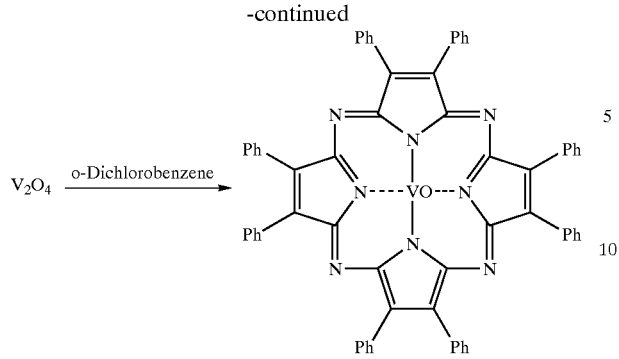

50 parts by weight of metal-free octaphenyl tetrazaporphyrine and 1.5 parts by weight of anhydrous vanadium oxide were refluxed for 1.5 hours in 25 parts by weight of o-dichlorobenzene. After the reaction was completed, the hot reaction mixture was filtered before the reaction mixture was cooled. The resulting solid product was washed with hot water and ethanol, and then extracted using chlorobenzene. Next, the resulting product was crystalized to obtain pure vanadium oxide octaphenyl tetrazaporphyrazine.

SYNTHESIS EXAMPLE 8

Manganese Octaphenyl Tetrazaporphyrazine

Manganese oxide octaphenyl tetrazaporphyrazine was synthesized as follows by the method disclosed in *J. Am. Soc.*, 4839 (1952).

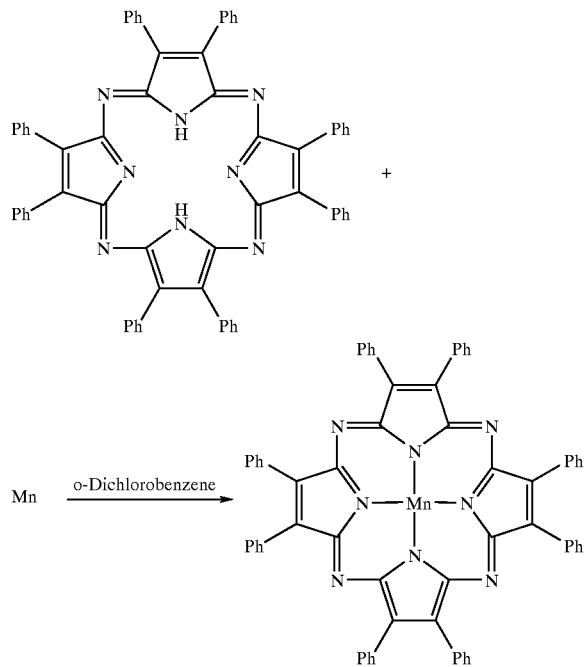

50 parts by weight of metal-free octaphenyl tetrazaporphyrine and 1.5 parts by weight of anhydrous manganese were refluxed for 1.5 hours in 25 parts by weight of o-dichlorobenzene. After the reaction was completed, the hot reaction mixture was filtered before the reaction mixture was cooled. The resulting solid product was washed with hot water and ethanol, and then extracted using chlorobenzene. Next, the resulting product was crystalized to obtain pure manganese oxide octaphenyl tetrazaporphyrazine.

Besides the above synthesis examples, compounds having the following formulae were synthesized in a similar manner as those of the synthesis examples.

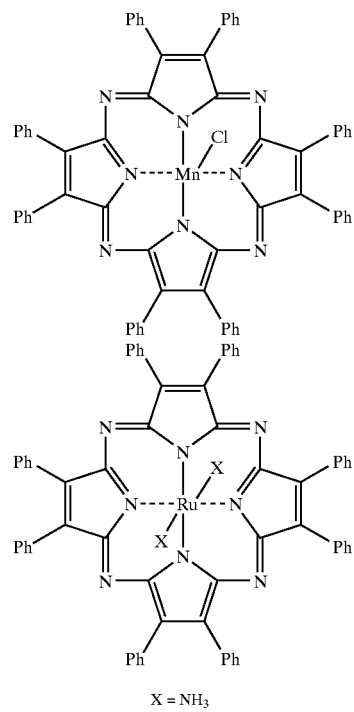

X = NH$_3$

EXAMPLE 1

Step 1: Preparation of Selectively Light-Absorptive Coating Composition for Displays 100 ml of methyl ethylketone (MEK) was placed in a reactor, and 30 g of polymethyl methacrylate was added into the reactor and dissolved while heating the reactor. Next, 10 mg of the octaphenyl tetrazaporphyrine obtained in Synthesis Example 1 was added to the mixture and dissolved. Then, 12 mg of Acridine Orange (manufactured by Aldrich Chemical Co.) was dissolved in 5 ml of isopropylalcohol, and the resultant solution was slowly added to the mixture containing the octaphenyl tetrazaporphyrine, thereby resulting in a selectively light-absorptive coating composition for displays.

Step 2: Manufacture of Filter for Displays

The coating composition obtained in Step 1 was spin coated on a transparent glass substrate, and dried at 90° C. for 10 minutes, so that a colored glass substrate with a colored layer having a thickness of 6 μm was manufactured. The colored glass substrate was mounted on a CRT and a PDP, and then the chromaticity coordinates for the three principal colors were measured. The ratio of each of the contrast and the brightness ratios, before and after combination with each display, was measured with respect to light emitted from the CRT and PDP. The results are shown in Table 1.

Figure 8:
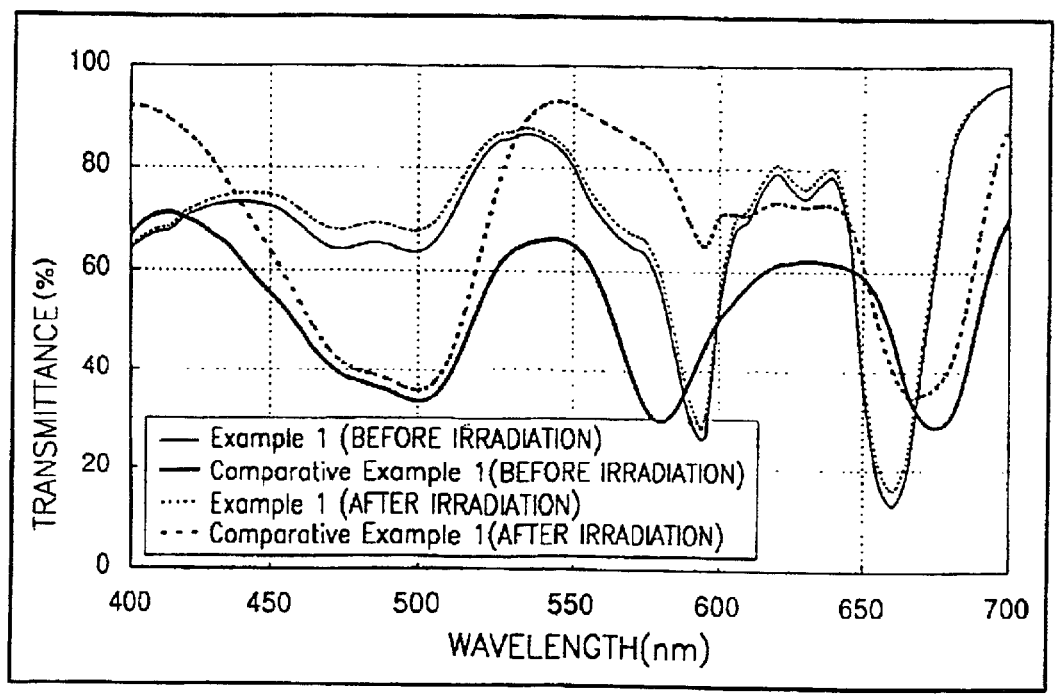
FIG. 8 comparatively shows the transmission spectra of colored glass substrates before and after irradiation, which were coated with the selectively light-absorptive coating compositions obtained in Example 1 and Comparative Example 1, respectively, according to the present invention.
Figure 11:
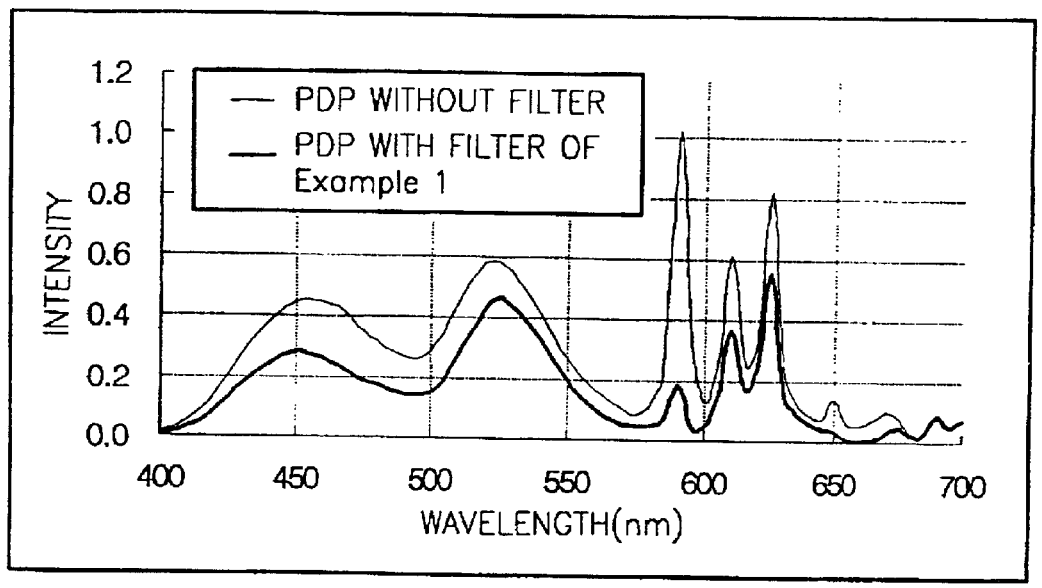
FIG. 11 comparatively shows the emission spectra for a PDP before and after a glass substrate colored with the selectively light-absorptive coating composition of Example 1 is combined with the PDP.

To evaluate light resistance of the colored glass substrate, a polyethylene terephtalate film, which acted as an anti-reflective film, was adhered to the colored glass substrate, and was irradiated with a xenon lamp of 2 kW for 3 hours. Transmittance before and after the irradiation was measured by a spectrophotometer. The transmittance of the colored glass substrate coated with the selectively light-absorptive coating composition according to the present invention, before and after the irradiation, is shown in FIG. 8. FIG. 11 shows the emission spectra of the PDP before and after the glass substrate coated with the coating composition from Example 1 is combined with the PDP.

EXAMPLE 2

Step 1: Preparation of Selectively Light-Absorptive Coating Composition for Displays 100 ml of MEK was placed in a reactor, and 30 g of polymethyl methacrylate was added into the reactor and dissolved while heating the reactor. Next, 8 mg of the octaphenyl tetrazaporphyrine obtained in Synthesis Example 1 and 150 mg of IRG022 (manufactured by NIPPON KAYAHU Co., Ltd.) were added to the mixture and dissolved. Then, 10 mg of of Acridine Orange (manufactured by Aldrich Chemical Co.) was dissolved in 5 ml of isopropyl alcohol, and the resultant solution was slowly added to the mixture containing the octaphenyl tetrazaporphyrine, thereby resulting in a selectively light-absorptive coating composition for displays.

Step 2: Manufacture of Filter for Displays

Figure 9:
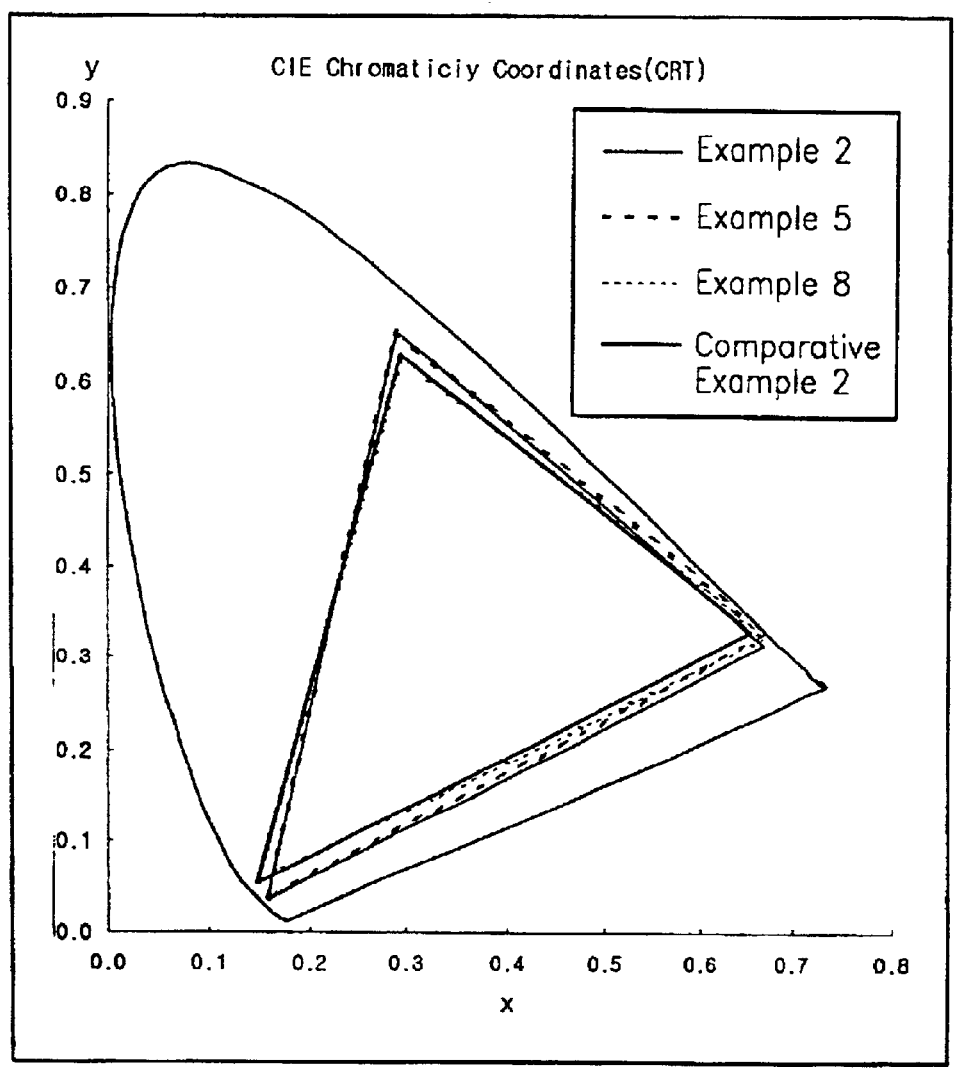
FIG. 9 comparatively shows the chromaticity coordinates for glass substrate of three principal colors, which were colored with the selectively light-absorptive coating compositions obtained in Examples 2, 5 and 8, and Comparative Example 2, and combined with a CRT.
Figure 10:
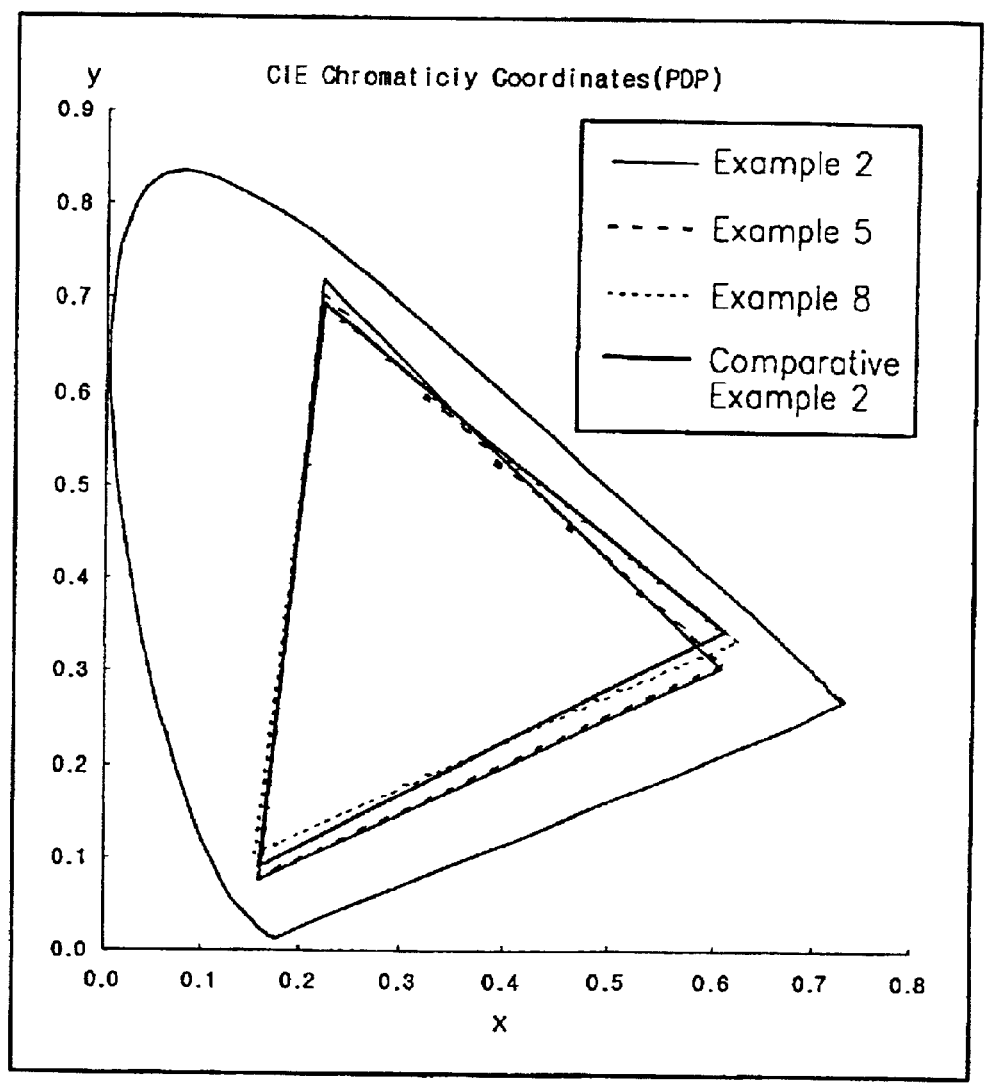
FIG. 10 comparatively shows the chromaticity coordinates for glass substrate of three principal colors, which were colored with the selectively light-absorptive coating compositions obtained in Examples 2, 5 and 8, and Comparative Example 2, and combined with a PDP.

A colored glass substrate with a colored layer having a thickness of about 6 μm was prepared in the same manner as in Example 1, using the coating composition obtained in Step 1 of the present example. The colored glass substrate was mounted on a CRT and a PDP, and then the chromaticity coordinates for the three principal colors were measured. The ratio of each of the contrast and the brightness, before and after combination with each display, was measured with respect to light emitted from the CRT and PDP. The results are shown in FIGS. 9 and 10, and Table 1.

EXAMPLE 3

Step 1: Preparation of Selectively Light-Absorptive Coating Composition for Displays A selectively light-absorptive coating composition was prepared in the same manner as in Example 2, except that IRG022 was replaced by 100 mg of Q-1 (manufactured by NIPPON KANKOH SHIKISO KENKYUSHO).

Step 2: Manufacture of Filter for Displays

A colored glass substrate with a colored layer having a thickness of about 6 μm was prepared in the same manner as in Example 1, using the coating composition obtained in Step 1 of the present example. The colored glass substrate was mounted on a CRT and a PDP, and then the chromaticity coordinates for the three principal colors were measured. The ratio of each of the contrast and the brightness, before and after combination with each display, was measured with respect to light emitted from the CRT and PDP. The results are shown in Table 1.

EXAMPLE 4

Step 1: Preparation of Selectively Light-Absorptive Coating Composition for Displays 100 ml of MEK was placed in a reactor, and 30 g of polymethyl methacrylate was added into the reactor and dissolved while heating the reactor. Next, 10 mg of the tribenzyl tetrazaporphyrine obtained in Synthesis Example 2 was added to the mixture and dissolved. Then, 12 mg of Acridine Orange (manufactured by Aldrich Chemical Co.) was dissolved in 5 ml of isopropylalcohol, and the resultant solution was slowly added to the mixture containing the tribenzyl tetrazaporphyrine, thereby resulting in a selectively light-absorptive coating composition for displays.

Step 2: Manufacture of Filter for Displays

Figure 12:
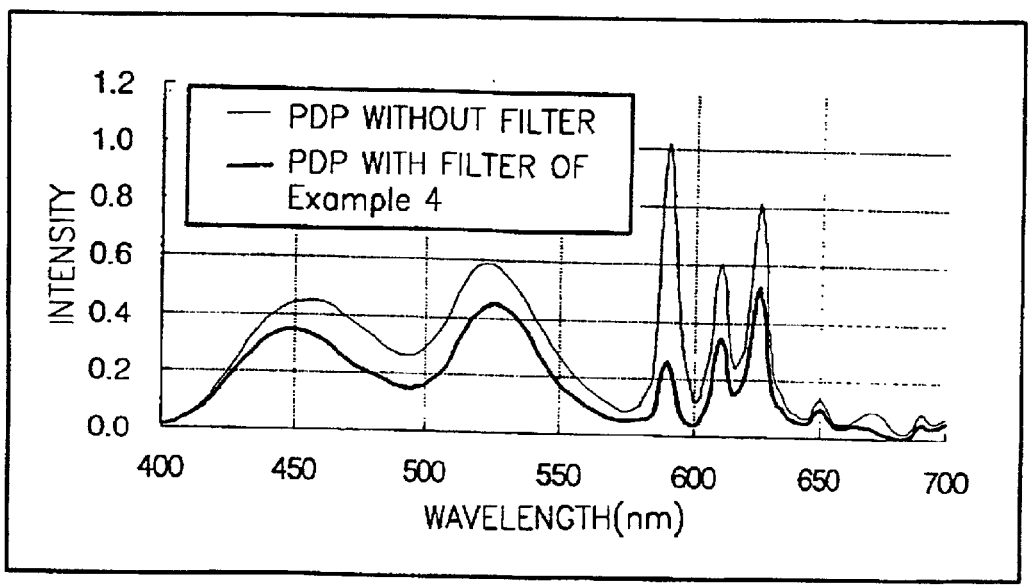
FIG. 12 comparatively shows the emission spectra for a PDP before and after a glass substrate colored with the selectively light-absorptive coating composition of Example 4 is combined with the PDP.

A colored glass substrate with a colored layer having a thickness of about 6 μm was prepared in the same manner as in Example 1, using the coating composition obtained in Step 1 of the present example. The colored glass substrate was mounted on a CRT and a PDP, and then the chromaticity coordinates for the three principal colors were measured. The ratio of each of the contrast and the brightness, before and after combination with each display, was measured with respect to light emitted from the CRT and PDP. The results are shown in Table 1. In addition, the emission spectra of the PDP before and after the mounting of the colored glass substrate were measured. The results are shown in FIG. 12.

EXAMPLE 5

Step 1: Preparation of Selectively Light-Absorptive Coating Composition for Displays 100 ml of MEK was placed in a reactor, and 30 g of polymethyl methacrylate was added into the reactor and dissolved heating the reactor. Next, 8 mg of the tribenzyl tetrazaporphyrine obtained in Synthesis Example 2 and 150 mg of IRG022 (manufactured by NIPPON KAYAHU Co., Ltd.) were added to the mixture and dissolved. Then, 10 mg of Acridine Orange (manufactured by Aldrich Chemical Co.) was dissolved in 5 ml of isopropyl alcohol, and the resulting solution was slowly added to the mixture containing the tribenzyl tetrazaporphyrine, thereby resulting in a selectively light-absorptive coating composition for displays.

Step 2: Manufacture of Filter for Displays

A colored glass substrate with a colored layer having a thickness of about 6 μm was prepared in the same manner as in Example 1, using the coating composition obtained in Step 1 of the present example. The colored glass substrate was mounted on a CRT and a PDP, and then the chromaticity coordinates for the three principal colors were measured. The ratio of each of the contrast and the brightness, before and after combination with each display, was measured with respect to light emitted from the CRT and PDP. The results are shown in FIGS. 9 and 10, and Table 1.

EXAMPLE 6

Step 1: Preparation of Selectively Light-Absorptive Coating Composition for Displays A selectively light-absorptive coating composition was prepared in the same manner as in Example 5, except that IRG022 was replaced by 100 mg of Q-1 (manufactured by NIPPON KANKOH SHIKISO KENKYUSHO).

Step 2: Manufacture of Filter for Displays

A colored glass substrate with a colored layer having a thickness of about 6 μm was prepared in the same manner as in Example 1, using the coating composition obtained in Step 1 of the present example. The colored glass substrate was mounted on a CRT and a PDP, and then the chromaticity coordinates for the three principal colors were measured. The ratio of each of the contrast and the brightness, before and after combination with each display, was measured with respect to light emitted from the CRT and PDP. The results are shown in Table 1.

EXAMPLE 7

Step 1: Preparation of Selectively Light-Absorptive Coating Composition for Displays 75 ml of toluene was placed in a reactor, and 25 g of polymethyl methacrylate was added into the reactor and dissolved while heating the reactor. Next, 30 mg of the ruthenium octaphenyl tetrazaporphyrine obtained in Synthesis Example 3 was added to the mixture and dissolved, thereby resulting in a selectively light-absorptive coating composition for displays.

Step 2: Manufacture of Filter for Displays

Figure 13:
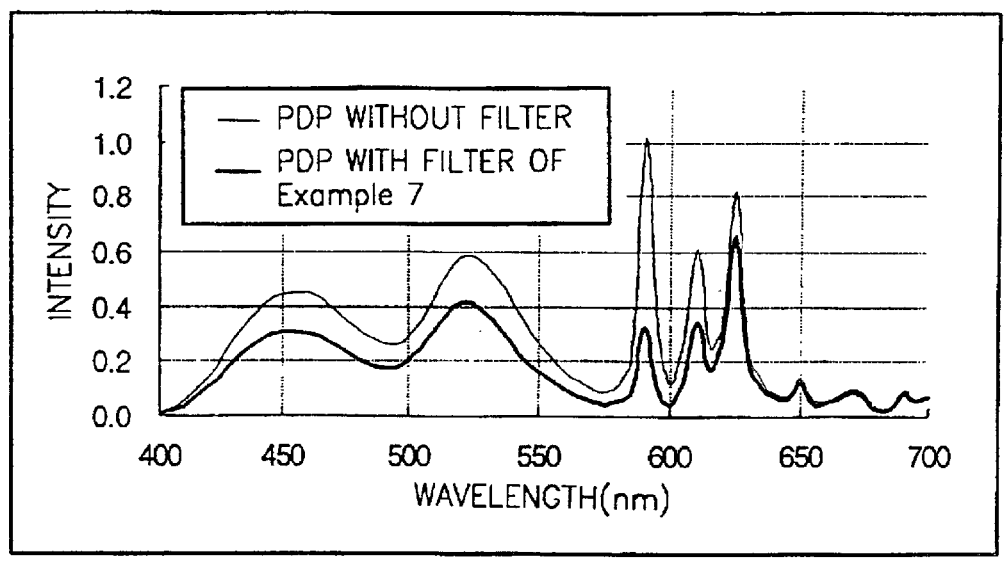
FIG. 13 comparatively shows the emission spectra for a PDP before and after a glass substrate colored with the selectively light-absorptive coating composition of Example 7 is combined with the PDP.

A colored glass substrate with a colored layer having a thickness of about 6 μm was prepared in the same manner as in Example 1, using the coating composition obtained in Step 1 of the present example. The colored glass substrate was mounted on a CRT and a POP, and then the chromaticity coordinates for the three principal colors were measured. The ratio of each of the contrast and the brightness, before and after combination with each display, was measured with respect to light emitted from the CRT and POP. The results are shown in Table 1. In addition, the emission spectra of the POP before and after the mounting of the colored glass substrate were measured. The results are shown in FIG. 13.

EXAMPLE 8

Step 1: Preparation of Selectively Light-Absorptive Coating Composition for Displays 75 ml of toluene was placed in a reactor, and 25 g of polymethyl methacrylate was added into the reactor and dissolved while heating the reactor. Next, 30 mg of the ruthenium octaphenyl tetrazaporphyrine obtained in Synthesis Example 3 and 150 mg of IRG022 (manufactured by NIPPON KAYAHU Co., Ltd.) were added to the mixture and dissolved. Then, 5 mg of Acridine Orange (manufactured by Aldrich Chemical Co.) was dissolved in 5 ml of isopropyl alcohol, and the resulting solution was slowly added to the mixture containing the ruthenium octaphenyl tetrazaporphyrazine, thereby resulting in a selectively light-absorptive coating composition for displays.

Step 2: Manufacture of Filter for Displays

A colored glass substrate with a colored layer having a thickness of about 6 μm was prepared in the same manner as in Example 1, using the coating composition obtained in Step 1 of the present example. The colored glass substrate was mounted on a CRT and a PDP, and then the chromaticity coordinates for the three principal colors were measured. The ratio of each of the contrast and the brightness, before and after combination with each display, was measured with respect to light emitted from the CRT and PDP. The results are shown in FIGS. 9 and 10, and Table 1.

EXAMPLE 9

Step 1: Preparation of Selectively Light-Absorptive Coating Composition for Displays A selectively light-absorptive coating composition was prepared in the same manner as in Example 8, except that IRG022 was replaced by 100 mg of Q-1 (manufactured by NIPPON KANKOH SHIKISO KENKYUSHO).

Step 2: Manufacture of Filter for Displays

A colored glass substrate with a colored layer having a thickness of about 6 μm was prepared in the same manner as in Example 1, using the coating composition obtained in Step 1 of the present example. The colored glass substrate was mounted on a CRT and a PDP, and then the chromaticity coordinates for the three principal colors were measured. The ratio of each of the contrast and the brightness, before and after combination with each display, was measured with respect to light emitted from the CRT and PDP. The results are shown in Table 1.

EXAMPLE 10

Step 1: Preparation of Selectively Light-Absorptive Coating Composition for Displays 75 ml of toluene was placed in a reactor, and 25 g of polymethyl methacrylate was added into the reactor and dissolved while heating the reactor. Next, 30 mg of the copper tetramethyl tetrazaporphyrazine obtained in Synthesis Example 4 and 150 mg of IRG022 (manufactured by NIPPON KAYAHU Co., Ltd.) were added to the mixture and dissolved. Then, 5 mg of Acridine Orange (manufactured by Aldrich Chemical Co.) was dissolved in 5 ml of isopropyl alcohol, and the resulting solution was slowly added to the mixture containing the copper tetramethyl tetrazaporphyrazine, thereby resulting in a selectively light-absorptive coating composition for displays.

Step 2: Manufacture of Filter for Displays

Figure 14:
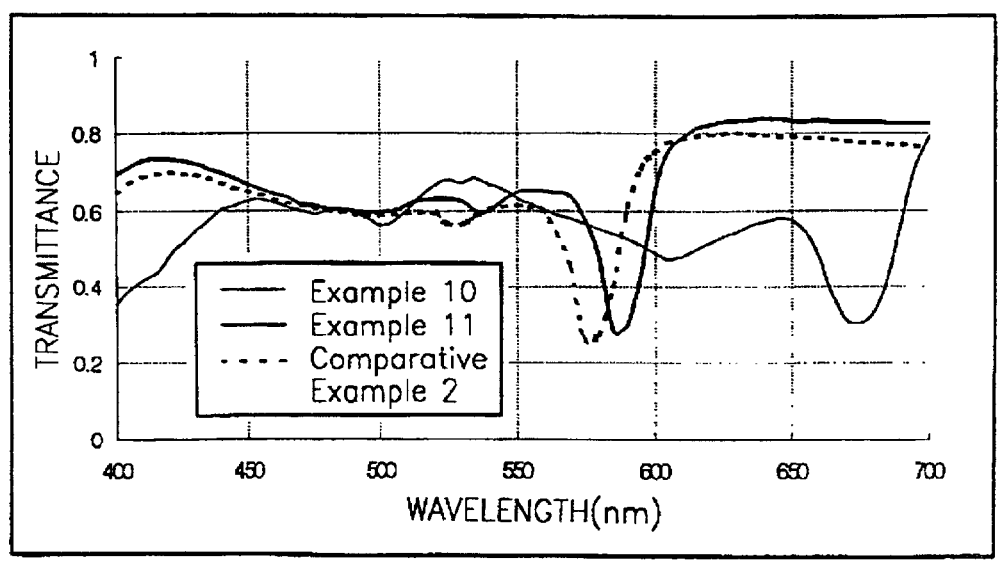
FIG. 14 is the transmission spectra of the glass substrates colored in Example 10 and 11, and Comparative Example 2 according to the present invention.

A colored glass substrate with a colored layer having a thickness of about 6 μm was prepared in the same manner as in Example 1, using the coating composition obtained in Step 1 of the present example. The colored glass substrate was mounted on a CRT and a PDP, and then the chromaticity coordinates for the three principal colors were measured. The ratio of each of the contrast and the brightness, before and after combination with each display, was measured with respect to light emitted from the CRT and PDP. The results are shown in Table 1. In addition, the transmission spectrum of the colored glass substrate was measured using a spectrophotometer. The result is shown in FIG. 14.

EXAMPLE 11

Step 1: Preparation of Selectively Light-Absorptive Coating Composition for Displays 75 ml of toluene was placed in a reactor, and 25 g of polymethyl methacrylate was added into the reactor and dissolved while heating the reactor. Next, 30 mg of the nickel tetramethyl tetrazaporphyrazine obtained in Synthesis Example 5 and 150 mg of IRG022 (manufactured by NIPPON KAYAHU Co., Ltd.) were added to the mixture and dissolved. Then, 5 mg of Acridine Orange (manufactured by Aldrich Chemical Co.) was dissolved in 5 ml of isopropyl alcohol, and the resulting solution was slowly added to the mixture containing the nickel tetramethyl tetrazaporphyrazine, thereby resulting in a selectively light-absorptive coating composition for displays.

Step 2: Manufacture of Filter for Displays

A colored glass substrate with a colored layer having a thickness of about 6 μm was prepared in the same manner as in Example 1, using the coating composition obtained in Step 1 of the present example. The colored glass substrate was mounted on a CRT and a PDP, and then the chromaticity coordinates for the three principal colors were measured. The ratio of each of the contrast and the brightness, before and after combination with each display, was measured with respect to light emitted from the CRT and PDP. The results are shown in Table 1. In addition, the transmission spectrum of the colored glass substrate was measured using a spectrophotometer. The result is shown in FIG. 14.

COMPARATIVE EXAMPLE 1

20 g of polyvinyl alcohol was dissolved in 100 ml of water, and 12 mg of Fluoresceinamine isomer I (manufactured by Aldrich Chemical Co.), 10 gm of Phloxin B (manufactured by Aldrich Chemical Co.), 5 mg of Sulforhodiamine 101 (manufactured by Aldrich Chemical Co.) and 13.5 mg of Luxol Fast Blue (manufactured by Aldrich Chemical Co.) were dissolved in the mixture. The obtained composition was spin coated on a transparent glass substrate and dried at 50° C. for 1 hour to deposit a colored layer having a thickness of about 8 μm. Applicability of the obtained colored glass substrate to CRTs and PDPs was evaluated in terms of the same characteristics measured in Example 1, by the same methods. The results are shown in Table 1.

In addition, light resistance of the colored glass substrate was measured in the same way as in Example 1. A change in transmittance before and after the irradiation was measured. The result is shown in FIG. 8. FIG. 8 shows that the colored glass substrate prepared in Comparative Example 1 exhibits a sudden change in transmittance in the region between green emission and red emission spectra due to photo decomposition of pigments blocking light in the corresponding region.

COMPARATIVE EXAMPLE 2

A selectively light-absorptive coating composition was prepared in the same way as in Example 11, except that 8 mg of Eastwell 590 (manufactured at by Eastwell Co.) was used instead of the nickel tetramethyltetrazaporphyrazine. Next, a colored glass substrate was prepared using the coating composition obtained in the present comparative example. The colored glass substrate was mounted on a CRT and a PDP, and then the is chromaticity coordinates for the three principal colors were measured. The ratio of each of the contrast and the brightness, before and after combination with each display, was measured with respect to light emitted from the CRT and PDP. The results are shown in FIGS. 9 and 10, and Table 1. In addition, the transmission spectrum of the colored glass substrate was measured using a spectrophotometer. The result is shown in FIG. 14.

TABLE 1

| Display | Example | CIE chromaticity coordinates (x, y) | | | Cr | Er | Cr × Er |
| --- | --- | --- | --- | --- | --- | --- | --- |
| | | Red | Green | Blue | | | |
| CRT | No filter | (0.653, 0.338) | (0.315, 0.611) | (0.146, 0.057) | — | — | — |
| | Example 1 | (0.668, 0.318) | (0.262, 0.672) | (0.153, 0.058) | 1.46 | 1.78 | 1.14 |
| | Example 2 | (0.667, 0.315) | (0.287, 0.655) | (0.157, 0.036) | 1.68 | 1.71 | 1.13 |
| | Example 3 | (0.670, 0.305) | (0.285, 0.665) | (0.147, 0.054) | 1.60 | 0.69 | 1.11 |
| | Example 4 | (0.660, 0.325) | (0.262, 0.672) | (0.153, 0.058) | 1.56 | 0.73 | 1.14 |
| | Example 5 | (0.667, 0.329) | (0.287, 0.655) | (0.157, 0.036) | 1.68 | 0.67 | 1.13 |
| | Example 6 | (0.670, 0.325) | (0.285, 0.665) | (0.147, 0.054) | 1.68 | 0.68 | 1.14 |
| | Example 7 | (0.667, 0.323) | (0.288, 0.628) | (0.147, 0.056) | 1.71 | 0.60 | 1.02 |
| | Example 8 | (0.667, 0.324) | (0.294, 0.627) | (0.147, 0.056) | 1.73 | 0.60 | 1.04 |
| | Example 9 | (0.663, 0.328) | (0.298, 0.622) | (0.147, 0.057) | 1.73 | 0.60 | 1.04 |
| | Example 10 | (0.663, 0.329) | (0.312, 0.611) | (0.148, 0.053) | 1.70 | 0.60 | 1.02 |
| | Example 11 | (0.668, 0.323) | (0.310, 0.616) | (0.148, 0.053) | 1.70 | 0.60 | 1.04 |
| | Comparative Example 1 | (0.667, 0.319) | (0.263, 0.678) | (0.155, 0.060) | 1.64 | 0.70 | 1.15 |
| | Comparative Example 2 | (0.654, 0.330) | (0.291, 0.628) | (0.147, 0.054) | 1.68 | 0.62 | 1.04 |
| PDP | No filter | (0.608, 0.353) | (0.236, 0.684) | (0.157, 0.107) | — | — | — |

TABLE 1-continued

| Display | Example | CIE chromaticity coordinates (x, y) | | | Cr | Er | Cr × Er |
| --- | --- | --- | --- | --- | --- | --- | --- |
| | | Red | Green | Blue | | | |
| | Example 1 | (0.608, 0.314) | (0.213, 0.730) | (0.162, 0.076) | 1.48 | 0.75 | 1.11 |
| | Example 2 | (0.607, 0.305) | (0.220, 0.720) | (0.162, 0.076) | 1.49 | 0.69 | 1.03 |
| | Example 3 | (0.618, 0.310) | (0.215, 0.730) | (0.166, 0.080) | 1.56 | 0.67 | 1.05 |
| | Example 4 | (0.608, 0.314) | (0.213, 0.730) | (0.162, 0.076) | 1.58 | 0.70 | 1.11 |
| | Example 5 | (0.607, 0.310) | (0.220, 0.705) | (0.162, 0.076) | 1.51 | 0.69 | 1.04 |
| | Example 6 | (0.618, 0.315) | (0.215, 0.710) | (0.166, 0.080) | 1.54 | 0.68 | 1.05 |
| | Example 7 | (0.619, 0.331) | (0.218, 0.696) | (0.154, 0.102) | 1.73 | 0.60 | 1.04 |
| | Example 8 | (0.620, 0.334) | (0.222, 0.695) | (0.155, 0.104) | 1.74 | 0.60 | 1.05 |
| | Example 9 | (0.617, 0.338) | (0.225, 0.692) | (0.155, 0.105) | 1.77 | 0.60 | 1.06 |
| | Example 10 | (0.619, 0.345) | (0.233, 0.685) | (0.158, 0.098) | 1.90 | 0.60 | 1.14 |
| | Example 11 | (0.626, 0.331) | (0.233, 0.687) | (0.157, 0.099) | 1.67 | 0.60 | 1.00 |
| | Comparative Example 1 | (0.606, 0.317) | (0.205, 0.732) | (0.160, 0.074) | 1.62 | 0.68 | 1.10 |
| | Comparative Example 2 | (0.610, 0.345) | (0.223, 0.695) | (0.161, 0.090) | 1.63 | 0.57 | 0.93 |

In Table 1, Cr and Er indicate the ratios of contrast and brightness, respectively, of the colored glass substrate, before and after the installation on a CRT or PDP. As shown in Table 1, the selectively light-absorptive coating compositions according to the present invention, which are coated on a glass substrate and combined with a color display, show improved chromaticity coordinates and contrast, compared to the coating compositions containing conventional light-absorptive materials.

The coating composition containing the selectively light-absorptive coating material according to the present invention blocks emission of light reflected in a display, and light of the intermediate colors exclusive of the three principal colors, thereby enhancing color purity and contrast.

What is claimed is:

1. A selectively light-absorptive material for a color display, comprising a tetrazaporphyrine derivative having formula (1)

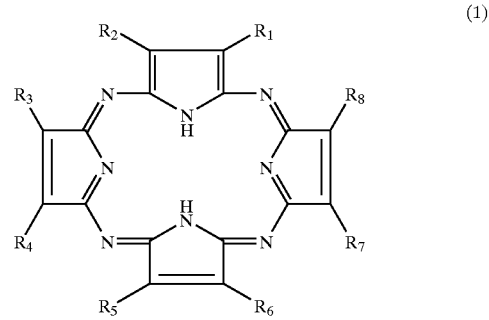

where $R_1$, $R_2$, $R_3$, $R_4$, $R_5$, $R_6$, $R_7$ and $R_8$ are independently selected from the group consisting of hydrogen; an unsubstituted phenyl group, an alkyl group of 1 to 8 carbon atoms; an alkoxy group of 1 to 8 carbon atoms; a nitro group; halogen atoms; a halide; a cyano group; an alkylamino group of 1 to 8 carbon atoms; an aminoalkyl group of 1 to 8 carbon atoms; and a phenyl group having a substitutent selected from an alkyl group of 1 to 8 carbon atoms, an alkoxy group of 1 to 8 carbon atoms, a nitro group, halogen atoms, a halide, an alkylamino group of 1 to 8 carbon atoms, an aminoalkyl group of 1 to 8 carbon atoms and a cyano group, or two neighboring substituents among $R_1$, $R_2$, $R_3$, $R_4$, $R_5$, $R_6$, $R_7$ and $R_8$ are fused and substituted with 1 to 3 aromatic cyclic compounds having formula (2a) through (2f), and unsubstituted groups among $R_1$, $R_2$, $R_3$, $R_4$, $R_5$, $R_6$, $R_7$ and $R_8$ are independently selected from the group consisting of hydrogen, an alkyl group of 1 to 8 carbon atoms, an alkoxy group of 1 to 8 carbon atoms, an allyl group, halogen atoms, a halide, a cyano group and a nitro group

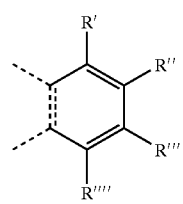

2a

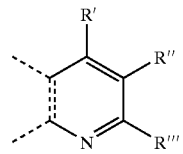

2b

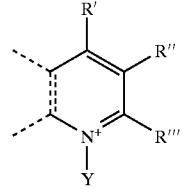

2c

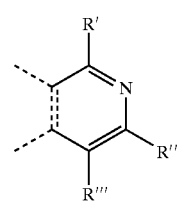

2d

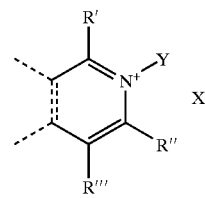

2e

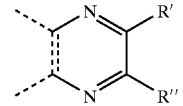

2f where R', R",R'" and R"" are independently selected from the group consisting of hydrogen, an alkyl group of 1 to 8 carbon atoms, an alkoxy group of 1 to 8 carbon atoms, an allyl group, a cyano group and a nitro group; X is halogen atoms or alkyl sulfonate of 1 to 8 carbon atoms; Y is an alkyl or allyl group of 1 to 8 carbon atoms; and dashed lines indicate a portion coupled with the pyrrole group of formula (1), a plastic resin; and an organic solvent selected from the group consisting of toluene, xylene, propylalcohol, isopropylalcohol, methylcellosolve, ethylcellosolve and dimethylformamide.

2. A selectively light-absorptive material for a color display, comprising a tetrazaporphyrine derivative having formula (1)

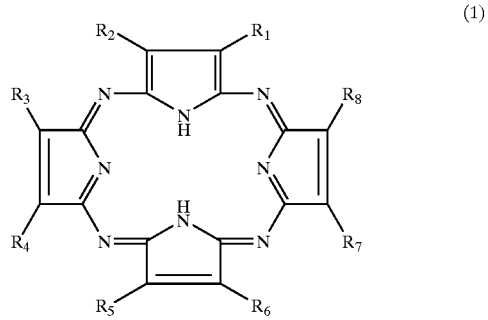

(1)

where $R_1$, $R_2$, $R_3$, $R_4$, $R_5$, $R_6$, $R_7$ and $R_8$ are independently selected from the group consisting of hydrogen; an unsubstituted phenyl group, an alkyl group of 1 to 8 carbon atoms; an alkoxy group of 1 to 8 carbon atoms; a nitro group; halogen atoms; a halide; a cyano group; an alkylamino group of 1 to 8 carbon atoms; an aminoalkyl group of 1 to 8 carbon atoms; and a phenyl group having a substitutent selected from an alkyl group of 1 to 8 carbon atoms, an alkoxy group of 1 to 8 carbon atoms, a nitro group, halogen atoms, a halide, an alkylamino group of 1 to 8 carbon atoms, an aminoalkyl group of 1 to 8 carbon atoms and a cyano group, or two neighboring substituents among $R_1$, $R_2$, $R_3$, $R_4$, $R_5$, $R_6$, $R_7$ and $R_8$ are fused and substituted with 1 to 3 aromatic cyclic compounds having formula (2a) through (2f), and unsubstituted groups among $R_1$, $R_2$, $R_3$, $R_4$, $R_5$, $R_6$, $R_7$ and $R_8$ are independently selected from the group consisting of hydrogen, an alkyl group of 1 to 8 carbon atoms, an alkoxy group of 1 to 8 carbon atoms, an allyl group, halogen atoms, a halide, a cyano group and a nitro group

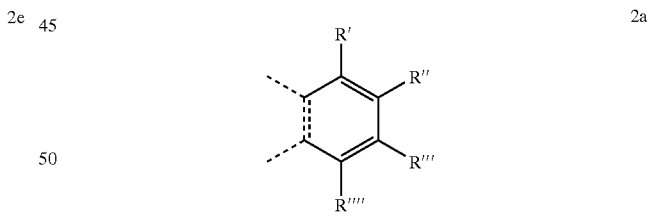

2a

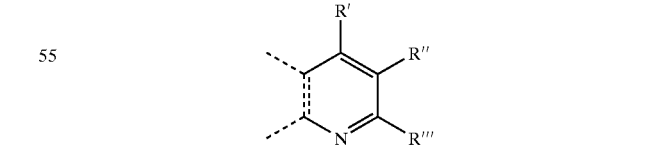

2b

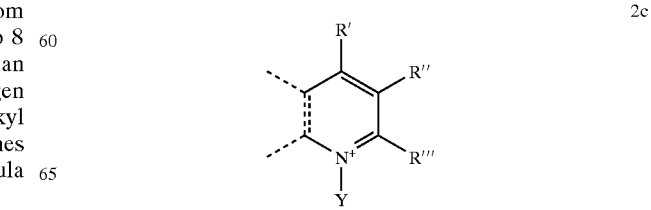

2c

-continued

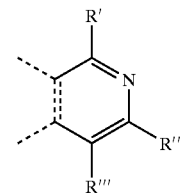
2d

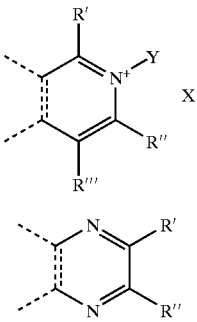
2e

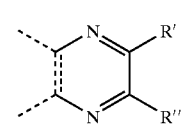
2f where R', R",R'" and R"" are independently selected from the group consisting of hydrogen, an alkyl group of 1 to 8 carbon atoms, an alkoxy group of 1 to 8 carbon atoms, an allyl group, a cyano group and a nitro group; X is halogen atoms or alkyl sulfonate of 1 to 8 carbon atoms; Y is an alkyl or allyl group of 1 to 8 carbon atoms; and dashed lines indicate a portion coupled with the pyrrole group of formula (1);

a plastic resin;
an organic solvent; and
an infrared ray blocking agent.

3. A selectively light-absorptive filter for a color display, comprising a tetrazaporphyrine derivative having formula (1)

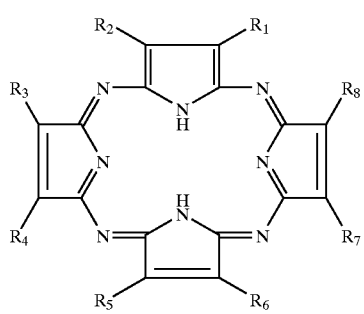
(1)

where $R_1$, $R_2$, $R_3$, $R_4$, $R_5$, $R_6$, $R_7$ and $R_8$ are independently selected from the group consisting of hydrogen; an unsubstituted phenyl group, an alkyl group of 1 to 8 carbon atoms; an alkoxy group of 1 to 8 carbon atoms; a nitro group; halogen atoms; a halide; a cyano group; an alkylamino group of 1 to 8 carbon atoms; an aminoalkyl group of 1 to 8 carbon atoms; and a phenyl group having a substitutent selected from an alkyl group of 1 to 8 carbon atoms, an alkoxy group of 1 to 8 carbon atoms, a nitro group, halogen atoms, a halide, an alkylamino group of 1 to 8 carbon atoms, an aminoalkyl group of 1 to 8 carbon atoms and a cyano group, or two neighboring substituents among $R_1$, $R_2$, $R_3$, $R_4$, $R_5$, $R_6$, $R_7$ and $R_8$ are fused and substituted with 1 to 3 aromatic cyclic compounds having formula (2a) through (2f), and unsubstituted groups among $R_1$, $R_2$, $R_3$, $R_4$, $R_5$, $R_6$, $R_7$ and $R_8$ are independently selected from the group consisting of hydrogen, an alkyl group of 1 to 8 carbon atoms, an alkoxy group of 1 to 8 carbon atoms, an allyl group, halogen atoms, a halide, a cyano group and a nitro group

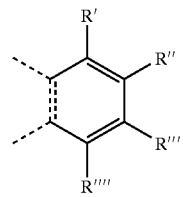
2a

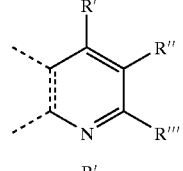
2b

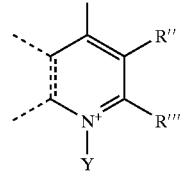
2c

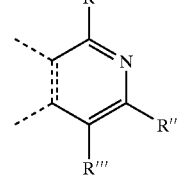
2d

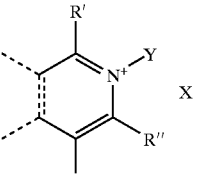
2e

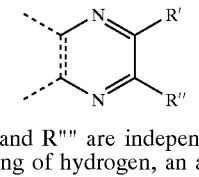
2f where R', R",R'" and R"" are independently selected from the group consisting of hydrogen, an alkyl group of 1 to 8 carbon atoms, an alkoxy group of 1 to 8 carbon atoms, an allyl group, a cyano group and a nitro group; X is halogen atoms or alkyl sulfonate of 1 to 8 carbon atoms; Y is an alkyl or allyl group of 1 to 8 carbon atoms; and dashed lines indicate a portion coupled with the pyrrole group of formula (1); and a plastic resin.

4. A selectively light-absorptive filter for a color display comprising the selectively light-absorptive material of claim 1.

5. A selectively light-absorptive filter for a color display comprising the selectively light-absorptive materal of claim 2.

6. The selectively light-absorptive filter of claim 3, wherein the plastic resin is at least one selected from the group consisting of poly(methylmethacrylate), polyvinyl alcohol, polycarbonate, ethylene vinylacetate and polyvinylbutyral.

* * * * *